United States Patent [19]
Gaugler et al.

[11] Patent Number: 5,939,526
[45] Date of Patent: Aug. 17, 1999

[54] ISOLATED RAGE-1 DERIVED PEPTIDES WHICH COMPLEX WITH HLA-B7 MOLECULES AND USES THEREOF

[75] Inventors: Beatrice Gaugler, Brussels; Benoit Van den Eynde, Rixensart, both of Belgium; Peter Schrier, Leiden; Nathalie Brouwenstijn, Oegstgeest, both of Netherlands; Thierry Boon-Falleur, Brussels, Belgium

[73] Assignee: Ludwig Institute for Cancer Research, New York, N.Y.

[21] Appl. No.: 08/530,569

[22] Filed: Sep. 20, 1995

Related U.S. Application Data

[63] Continuation-in-part of application No. 08/408,015, Mar. 21, 1995.

[51] Int. Cl.$^6$ .............................. C07K 7/00; C07K 7/06; A61K 38/08; A61K 38/04
[52] U.S. Cl. ...................... 530/328; 530/300; 530/350; 530/828; 530/395; 514/15; 514/2; 514/885; 424/184.1; 424/185.1; 424/277.1
[58] Field of Search .................. 424/184.1, 185.1, 424/277.1; 514/15, 2, 885; 530/300, 328, 350, 828, 395

[56] References Cited

U.S. PATENT DOCUMENTS

| | | | |
|---|---|---|---|
| 5,342,774 | 8/1994 | Boon et al. | 435/371 |
| 5,405,940 | 4/1995 | Boon et al. | 530/328 |

FOREIGN PATENT DOCUMENTS

WO 92/20356   11/1992   WIPO .

OTHER PUBLICATIONS

Gieser et al., Genomics, 13:873–876, 1992.
van der Bruggen et al., A Gene Encoding an Antigen Recognized by Cytolytic Lymphocytes on a Human Melanoma, Science 254: 1643–1647, 1991.
Khanna et al., Localization of Epstein–Barr Virus Cytotoxic T Cell Epitopes Using Recombinant Vaccinia: Implications for Vaccine Development, J. Exp. Med. 176:169–176, 1992.
Koo et al., Autologous Tumor–Specific Cytotoxicity of Tumor–Infiltrating Lymphocytes Derived from Human Renal Cell Carcinoma, J. Immunotherapy 10:347–354, 1991.
Schendel et al., Tumor–Specific Lysis of Human Renal Cell Carcinomas by Tumor–Infiltrating Lymphocytes, J. Immunology 151:4209–4220, 1993.
Van den Eynde et al., New tumor antigens recognized by T cells. Curr. Opinion in Immun. 7:674–681, 1995.
Choudhary et al., Selective lysis of autologous tumor cells by recurrent γδ tumor–infiltrating lymphocytes from renal carcinoma. J. Immunol. 154: 3932, 1995.
Van den Eynde et al., Presence on a Human Melanoma of Multiple Antigens Recognized by Autologous Ctl. Int. J. Cancer:44, 634–640, 1989.
Rammensee, et al., MHC ligands andpeptide motifs: first listing. Immunogenetics 41: 178–228, 1995.

*Primary Examiner*—Ronald B. Schwadron
*Attorney, Agent, or Firm*—Wolf, Greenfield & Sacks, P.C.

[57] ABSTRACT

The invention describes the RAGE tumor rejection antigen precursor family, including nucleic acids encoding such tumor rejection antigen precursors, tumor rejection antigen peptides or precursors thereof and antibodies relating thereto. Methods and products also are provided for diagnosing and treating conditions characterized by expression of a RAGE tumor rejection antigen precursor.

3 Claims, 5 Drawing Sheets

ISOLATED RAGE-1 DERIVED PEPTIDES WHICH COMPLEX WITH HLA-B7 MOLECULES AND USES THEREOF

RELATED APPLICATION

This application is a continuation-in-part of U.S. patent application Ser. No. 08/408,015, filed on Mar. 21, 1995, pending entitled RAGE TUMOR REJECTION ANTIGEN PRECURSORS, the disclosure of which is incorporated herein by reference.

FIELD OF THE INVENTION

This invention relates to nucleic acid molecules which code for tumor rejection antigens and precursors thereof. The tumor rejection antigen precursors are processed, inter alia, into at least one tumor rejection antigen that is presented by HLA molecules. The nucleic acid molecules, proteins coded for by such molecules and peptides derived therefrom, as well as related antibodies and cytotoxic lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response. T cells can recognize and interact with other cells via cell surface complexes on the other cells of peptides and molecules referred to as human leukocyte antigens ("HLA") or major histocompatibility complexes ("MHCs"). The peptides are derived from larger molecules which are processed by the cells which also present the HLA/MHC molecule. See Male et al., *Advanced Immunology* (J. P. Lipincott Company, 1987), especially chapters 6–10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities.

The mechanism by which T cells recognize alien materials has also been implicated in cancer. For example, in PCT application PCT/US92/04354, filed May 22, 1992, published on Nov. 26, 1992, and incorporated herein by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774.

In U.S. patent application Ser. No. 938,334, now U.S. Pat. No. 5,405,940, incorporated herein by reference, nonapeptides are taught which are presented by the HLA-A1 molecule. Given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993, now abandoned and incorporated herein by reference, the fact that the MAGE-1 expression product is processed to a second TRA is disclosed. This second TRA is presented by HLA-C clone 10 molecules. Therefore, a given TRAP can yield a plurality of TRAs.

In U.S. patent application Ser. No. 994,928, filed Dec. 22, 1992, now abandoned and incorporated herein by reference, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. patent application Ser. No. 08/032,978, filed Mar. 18, 1993, now U.S. Pat. No. 5,620,88 and incorporated herein by reference, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 079,110, filed Jun. 17, 1993, now U.S. Pat. No. 5,571,711 and entitled "Isolated Nucleic Acid Molecules Coding For BAGE Tumor Rejection Antigen Precursors" and Ser. No. 196,630, filed Feb. 15, 1994, now U.S. Pat. No. 5,683,88 and entitled "Isolated Peptides Which Form Complexes with MHC Molecule HLA-C-Clone 10 and Uses Thereof", both of which are incorporated herein by reference, an unrelated tumor rejection antigen precursor, the so-called "BAGE" precursor, is described. TRAs are derived from the TRAP and also are described. They form complexes with MHC molecule HLA-C-Clone 10.

In U.S. patent application Ser. No. 096,039, filed Jul. 22, 1993, now abandoned and entitled "Isolated Nucleic Acid Molecules Coding for GAGE Tumor Rejection Antigen Precursors" and Ser. No. 250,162, filed May 27, 1994 now U.S. Pat. No. 5,610,013 and entitled "Method for Diagnosing a Disorder by Determining Expression of GAGE Tumor Rejection Antigen Precursors", both of which are incorporated herein by reference, another unrelated tumor rejection antigen precursor, the so-called "GAGE" precursor, is described. The GAGE precursor is not related to the BAGE or the MAGE family.

The work which is presented by the papers, patents and patent applications described above deal, for the most part, with the MAGE family of genes, the BAGE gene and the GAGE gene. It now has been discovered that another gene family, the "RAGE" genes, encode additional tumor rejection antigens and precursors thereof. The RAGE genes do not show homology to the MAGE family of genes, to the BAGE gene or the GAGE gene.

The invention is elaborated upon in the disclosure which follows.

SUMMARY OF THE INVENTION

The invention provides isolated nucleic acid molecules, expression vectors containing those molecules and host cells transfected with those molecules. The invention also provides isolated proteins and peptides, and antibodies to those proteins and peptides. Kits containing the foregoing molecules additionally are provided. The foregoing can be used in the diagnosis or treatment of conditions characterized by the expression of a RAGE TRA or TRAP.

According to one aspect of the invention, an isolated polypeptide is provided. It includes at least the amino acid sequence of SEQ.ID.NO.23 and is a RAGE TRA. In preferred embodiments, the isolated polypeptide includes at least the amino acid sequence of SEQ.ID.NO.26. In other embodiments the isolated polypeptide may consist essentially of or may even be only the amino acid sequence of SEQ.ID.NO.23 or SEQ.ID.NO.26.

According to another aspect of the invention, an isolated nucleic acid molecule is provided. The molecule encodes a polypeptide selected from the group consisting of SEQ.ID.NO.23 and SEQ.ID.NO.26. The isolated nucleic acid can include SEQ.ID.NO.27 and preferably includes SEQ.ID.NO.28. In other embodiments the isolated nucleic acid may consist essentially of or may even be only SEQ.ID.NOs.27 or 28.

According to another aspect of the invention, an isolated nucleic acid molecule is provided which hybridizes under stringent conditions to a molecule consisting of the nucleic acid sequence selected from the group consisting of SEQ.ID.NO.1, SEQ.ID.NO.2, SEQ.ID.NO.4, SEQ.ID.NO.6, SEQ.ID.NO.11, SEQ.ID. NO.12, SEQ.ID.NO.13, SEQ.ID.NO.14, SEQ.ID.NO.16, SEQ.ID.NO.18, AND SEQ.ID.NO.20. Such molecules code for RAGE TRAs or TRAPs, with the proviso that the isolated nucleic acid molecule does not code for a MAGE, GAGE or BAGE TRA or TRAP. In preferred embodiments, the isolated nucleic acid molecule is an mRNA molecule or a cDNA molecule. In one embodiment, the isolated nucleic acid molecule is complementary to nucleotides selected from the group consisting of 506 to 793 of SEQ.ID.NO.1, 627 to 848 of SEQ.ID.NO.1, 387 to 509 of SEQ.ID.NO.1, 273 to 449 of SEQ.ID.NO.11, 187 to 276 of SEQ.ID.NO.11, 269 to 832 of SEQ.ID.NO.13 and 369 to 557 of SEQ.ID.NO.13. In another embodiment, the isolated nucleic acid consists essentially of SEQ.ID.NO.1, SEQ.ID.NO.2, SEQ.ID. NO.4, SEQ.ID.NO.6, SEQ.ID.NO.11, SEQ.ID. NO.12, SEQ.ID.NO.13, SEQ.ID.NO.14, SEQ.ID.NO.16, SEQ.ID.NO.18, SEQ.ID.NO.20, SEQ.ID.NO.27 OR SEQ.ID.NO.28.

According to another aspect of the invention, expression vectors and host cells containing those expression vectors are provided. The expression vectors include any one or more of the isolated nucleic acid molecules described above. In one embodiment, the expression vector comprises the isolated nucleic acid of SEQ.ID.NOs.27 or 28. Other expression vectors according to the invention include the isolated nucleic acids described above and a nucleic acid which codes for an HLA molecule which can present the TRAs of the invention to cytolytic T cells. One example is HLA-B7. The host cells may endogenously express the HLA molecule such as HLA-B7.

According to another aspect of the invention, isolated nucleic acid molecules that are unique fragments of SEQ.ID.NO.1, SEQ.ID.NO.11, SEQ.ID.NO.12 or SEQ.ID.NO.13 or their complements are provided. Such unique fragments are used to identify or to selectively amplify the nucleic acids described above. When the unique fragments are used for identifying expression of the above nucleic acids, the unique fragments preferably are between 200 and 1310 nucleotides in length, 200 and 1234 nucleotides in length, 200 and 2050 nucleotides in length or 200 and 1167 nucleotides in length. When the unique fragments are used to amplify the above-described nucleic acid molecules, the unique fragments are between 12 and 32 nucleotides in length. It will be recognized that amplification procedures are not exclusive of procedures that might be used to identify a nucleic acid molecule.

According to another aspect of the invention, kits for detecting the presence of expression of a TRA or TRAP are provided. Such kits employ two or more of the above-described molecules isolated in separate containers and packaged in a single package. In one such kit, a pair of amplification primers are provided, each of the pair consisting essentially of a 12–32 in length nucleotide contiguous segment of SEQ.ID.NO.1 or the complement thereof, SEQ.ID.NO.11 or the complement thereof, SEQ.ID.NO.12 or the complement thereof, or SEQ.ID.NO.13 or the complement thereof, and wherein the contiguous segments are non-overlapping. Preferably the amplification primers are PCR primers, wherein one of the primers is a contiguous segment of the Watson strand and another of the primers is the complement of a contiguous segment of Crick strand. In certain embodiments, primers are constructed and arranged to selectively amplify or identify only one of the RAGE family, such as only RAGE 1 or a portion of only RAGE 1, etc. For example, one of the pair can be contiguous in RAGE 1 genes and allelic variants thereof but not contiguous in RAGE 2, 3 or 4 genes. More specifically, a first primer can be a nucleic acid consisting essentially of any one of SEQ.ID.NOs.30–37, and a second primer can consist essentially of a 12–32 in length nucleotide contiguous segment of SEQ.ID.NO.1, or the complement thereof, depending upon the choice of the first primer.

Another kit according to the invention is an expression kit comprising a separate portion of the isolated nucleic acid molecule which codes for a RAGE TRAP, or a molecule including a RAGE TRA, and an HLA presenting molecule that forms a complex with that TRA and that stimulates a cytolytic T cell response. One such kit includes a nucleic acid which codes for the peptide of SEQ.ID.NO.23 or SEQ.ID.NO.26 and a nucleic acid molecule which codes for HLA-B7. Another kit according to the invention is an expression kit comprising a separate portion of the isolated nucleic acid molecule which hybridizes under stringent conditions to a molecule consisting of the nucleic acid sequence selected from the group consisting of SEQ.ID.NO.1, SEQ.ID.NO.2, SEQ.ID.NO.4, and SEQ.ID.NO.6 and which codes for a RAGE TRAP, and a nucleic acid molecule which codes for HLA-B7.

According to another aspect of the invention isolated TRAPs coded for by the above molecules and useful fragments thereof also are provided. Antibodies to such molecules and to complexes of HLA and RAGE TRAs also are provided.

According to another aspect of the invention, methods for diagnosing a disorder characterized by expression of a RAGE TRAP are provided. One method involves a RAGE TRAP which is processed to a RAGE derived TRA that forms a complex with HLA molecules. The method involves contacting a biological sample isolated from a subject with an agent that binds the complex and then determining binding between the complex and the agent as a determination of the disorder. In one embodiment, the method determines binding of the agent to a complex of RAGE TRA and HLA-B7. In this embodiment, the RAGE TRA can be selected from the group consisting of the peptide of SEQ.ID.NO.23 and the peptide of SEQ.ID.NO.26. Another method involves contacting a biological sample isolated from a subject with an agent that is specific for a RAGE nucleic acid or an expression product thereof. Interaction between the agent and the nucleic acid or expression product thereof then is determined, interaction being indicative of the disorder. The agent may be a nucleic acid which hybridizes under stringent conditions to a molecule consisting of the nucleic acid sequence selected from the group consisting of SEQ.ID.NO.1, SEQ.ID.NO.2, SEQ.ID.NO.4, SEQ.ID.NO.6, SEQ.ID.NO.11, SEQ.ID. NO.12, SEQ.ID.NO.13, SEQ.ID.NO.14, SEQ.ID.NO.16, SEQ.ID.NO.18 and SEQ.ID.NO.20, and which codes for a TRAP, with the proviso that the isolated nucleic acid molecule does not code for a MAGE, GAGE, or BAGE TRAP. Another method involves contacting a biological sample isolated from a subject with an agent that is specific for a RAGE tumor rejection antigen peptide and then determining interaction between the peptide and the agent as a determination of the disorder. In one embodiment, the peptide is selected from the group consisting of SEQ.ID.NO.23 and SEQ.ID.NO.26.

According to another aspect of the invention, an isolated biological preparation is provided. The preparation consists essentially of cytolytic T cells specific for complexes of an HLA molecule and a RAGE TRA. In one embodiment, the cytolytic T cells are specific for complexes of an HLA-B7 molecule and the TRA. In this embodiment, the antigen can be a peptide selected from the group consisting of the peptide of SEQ.ID.NO.23 and the peptide of SEQ.ID.NO.26.

Another aspect of the invention thus involves a method for enriching selectively a population of T cells with cytolytic T cells specific for complexes of an HLA molecule and a RAGE TRA. The method involves contacting an isolated population of T cells containing cytolytic T cell precursors with an agent resulting in presentation of a complex of a RAGE TRA and HLA presenting molecule, in an amount sufficient to selectively enrich the isolated population of T cells with said cytolytic T cells. In one preferred embodiment, the HLA molecule is HLA-B7 and the RAGE TRA is selected from the group consisting of a peptide consisting of the amino acids of SEQ.ID.NO.23 and a peptide consisting of the amino acids of SEQ.ID.NO.26.

Still another aspect of the invention involves methods for treating a subject with a disorder characterized by expression of a RAGE TRA or TRAP. One such method involves administering to a subject in need of such treatment an effective amount of an agent which enriches selectively in the subject the presence of complexes of HLA and RAGE TRA, resulting in cytolytic T cell response reactive with such complexes, sufficient to ameliorate the disorder. Such agents include the RAGE TRAPs and recombinant cells expressing complexes of the HLA and RAGE TRA. In one embodiment, such agents include cells expressing a complex of HLA-B7 and a peptide consisting of the peptide of SEQ.ID.NO.23 or the peptide of SEQ.ID.NO.26. Another method involves administering to a subject in need of such treatment an amount of autologous cytolytic T cells sufficient to ameliorate the disorder, wherein the autologous cytolytic T cells are specific for complexes of an HLA molecule and a RAGE TRA.

These and other objects of the invention will be described in further detail in connection with the detailed description of the invention.

BRIEF DESCRIPTION OF THE SEQUENCES

Figure 5:
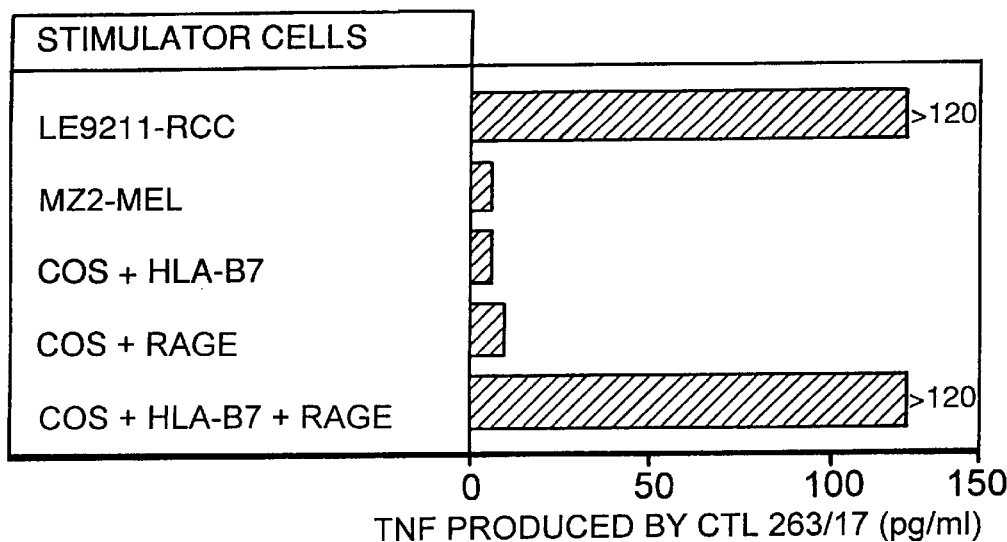
FIG. 5 is a graph showing the levels of tumor necrosis factor produced when CTL Clone 263/17 is combined with COS cells transfected with HLA-B7 cDNA and a cDNA encoding a RAGE TRAP.

SEQ.ID.NO.1 is the nucleotide sequence containing the RAGE tumor rejection antigen precursor mentioned in connection with FIG. 5.

SEQ.ID.NO.2 is open reading frame 2 (ORF2) of the cDNA of SEQ.ID.NO.1.

SEQ.ID.NO.3 is the translated amino acid sequence of SEQ.ID.NO.2.

SEQ.ID.NO.4 is open reading frame 3 (ORF3) of the cDNA of SEQ.ID.NO.1.

SEQ.ID.NO.5 is the translated amino acid sequence of SEQ.ID.NO.4.

SEQ.ID.NO.6 is open reading frame 1 (ORF1) of the cDNA of SEQ.ID.NO.1.

SEQ.ID.NO.7 is the translated amino acid sequence of SEQ.ID.NO.6.

SEQ.ID.NO.8 is a sense primer used in PCR tests for expression of the RAGE TRAP.

SEQ.ID.NO.9 is an antisense primer used in PCR tests for expression of the RAGE TRAP, common to all RAGE genes tested.

SEQ.ID.NO.10 is an antisense primer, specific for RAGE-1, used in PCR tests for expression of the RAGE-1 TRAP gene.

SEQ.ID.NO.11 is the nucleotide sequence of the RAGE-2 cDNA.

SEQ.ID.NO.12 is the nucleotide sequence of the RAGE-3 cDNA.

SEQ.ID.NO.13 is the nucleotide sequence of the RAGE-4 cDNA.

SEQ.ID.NO.14 is open reading frame 1' (ORF1') of the cDNAs of SEQ.ID.NOs.11, 12, and 13.

SEQ.ID.NO.15 is the translated amino acid sequence of SEQ.ID.NO.14.

SEQ.ID.NO.16 is open reading frame 4 (ORF4) of the cDNAs of SEQ.ID.NOs.11, and 12.

SEQ.ID.NO.17 is the translated amino acid sequence of SEQ.ID.NO.16.

SEQ.ID.NO.18 is open reading frame 4' (ORF4') of the cDNA of SEQ.ID.NO.13.

SEQ.ID.NO.19 is the translated amino acid sequence of SEQ.ID.NO.18.

SEQ.ID.NO.20 is open reading frame 2' (ORF2') of the cDNA of SEQ.ID.NO.13.

SEQ.ID.NO.21 is the translated amino acid sequence of SEQ.ID.NO.20.

Figure 8:
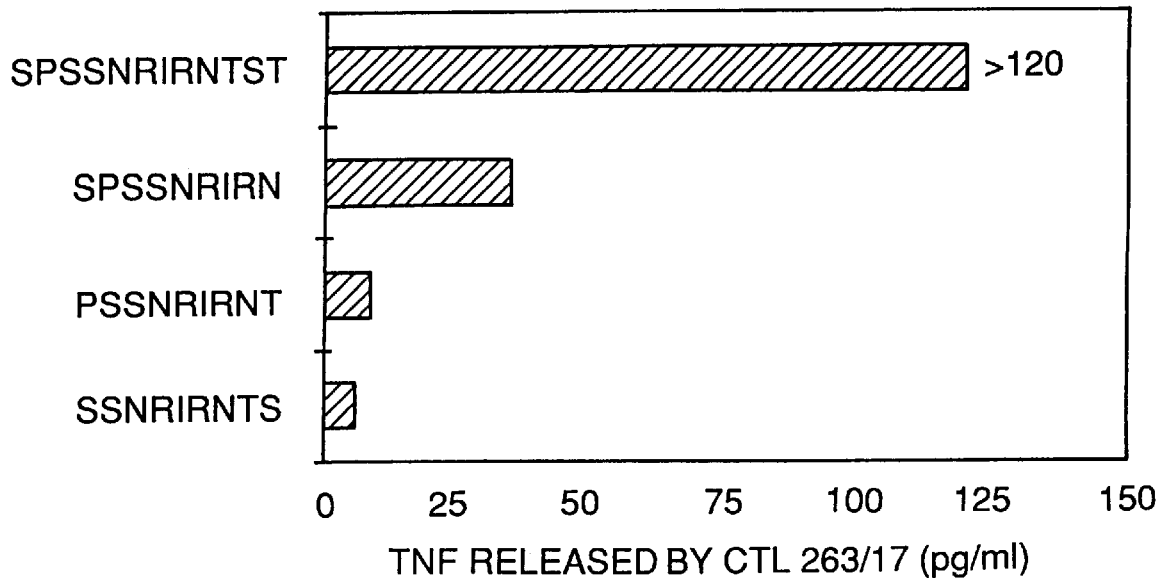
FIG. 8 is a graph detailing the levels of tumor necrosis factor produced when CTL Clone 263/17 is combined with peptide fragments of the TRAP encoded by ORF1 of the RAGE gene (SPSSNRIRNTST, SEQ ID NO:22; SPSSNRIRN, SEQ ID NO:23; PSSNRIRNT, SEQ ID NO:24; SSNRIRNTS, SEQ ID NO:25) and COS cells transfected with HLA-B7.

SEQ.ID.NO.22 is the dodecamer peptide containing the RAGE tumor rejection antigen mentioned in connection with FIG. 8.

SEQ.ID.NO.23 is a nonamer fragment (amino acids 1–9) of the peptide described in SEQ.ID.NO.22.

SEQ.ID.NO.24 is a nonamer fragment (amino acids 2–10) of the peptide described in SEQ.ID.NO.22.

SEQ.ID.NO.25 is a nonamer fragment (amino acids 3–11) of the peptide described in SEQ.ID.NO.22.

SEQ.ID.NO.26 is a decamer fragment (amino acids 1–10) of the peptide described in SEQ.ID.NO.22.

SEQ.ID.NO.27 is the nucleotide sequence of a DNA which encodes the peptide of SEQ.ID.NO.23.

SEQ.ID.NO.28 is the nucleotide sequence of a DNA which encodes the peptide of SEQ.ID.NO.26.

SEQ.ID.NO.29 represents the region of RAGE genes flanking the insertion point of ORF1, with the insertion designated by N.

SEQ.ID.NOs.30–37 are PCR primers useful in identification of RAGE 1.

DETAILED DESCRIPTION OF THE INVENTION

An antigen recognized on a renal cell carcinoma by autologous CTL restricted by HLA-B7 is encoded by a previously unknown gene. This gene is silent in all normal tissues (including testis), except for retina, and it is expressed in several tumor samples.

EXAMPLE 1

Description of an anti-renal cell carcinoma CTL clone of patient LE9211

Tumor line LE9211-RCC is a renal cell carcinoma line derived from a tumor sample of a female patient named LE9211. A sample thereof was irradiated, so as to render it non-proliferative. These irradiated cells were then used to isolate cytolytic T cell clones ("CTLs") specific thereto.

A sample of peripheral blood mononuclear cells ("PBMCs") was taken from patient LE 9211, and contacted to the irradiated carcinoma cells. After 14 days, the mixture was observed for lysis of the carcinoma cells, which indicated that CTLs specific for a complex of peptide and HLA molecule presented by the carcinoma cells were present in the sample.

The lysis assay employed was a chromium release assay following Herin et al., Int. J. Cancer 39:390–396 (1987). The assay, however, is briefly described herein. The target carcinoma cells were grown in vitro, and then resuspended at $10^7$ cells/ml in Dulbecco's Modified Eagles Medium (DMEM), supplemented with 30% FCS, and incubated for 45 minutes at 37° C. with 200 $\mu$uCi/ml of Na($^{51}$Cr)O$_4$. Labeled cells were washed three times with DMEM. These were then resuspended in DMEM supplemented with 10 mM Hepes and 10% fetal calf serum (FCS), after which 100 $\mu$l aliquots containing $10^3$ cells were distributed into 96 well microplates. Samples of lymphocytes were added in 100 $\mu$l of the same medium, and assays were carried out in duplicate. Plates were centrifuged for 4 minutes at 100 g and incubated for four hours at 37° C. in a 8% CO$_2$ atmosphere.

Plates were centrifuged again, and 100 $\mu$l aliquots of supernatant were collected and counted. Percentage of $^{51}$Cr release was calculated as follows:

$$\% \,^{51}CR\,\text{release} = \frac{(ER - SR)}{(MR - SR)} \times 100$$

where ER is observed, experimental $^{51}$Cr release, SR is spontaneous release measured by incubating $10^3$ labeled cells in 200 $\mu$l of medium alone, and MR is maximum release, obtained by adding 100 $\mu$l 0.3% Triton X-100 to target cells.

Those mononuclear blood samples which showed high CTL activity were expanded and cloned via limiting dilution, and were screened again, using the same methodology. A CTL clone was then isolated. The clone is referred to as 263/17 hereafter.

Figure 1:
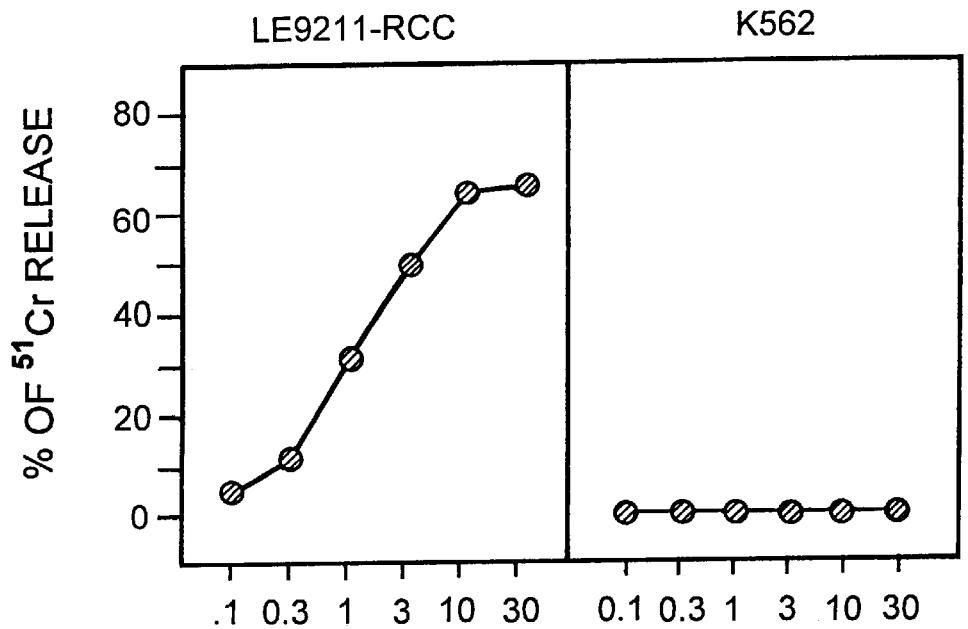
FIG. 1 is a graph detailing the lytic activity of CTL Clone 263/17 against autologous tumor LE9211-RCC cells compared with K562 control cells.

This clone was capable of lysing specifically the autologous tumor cells and not NK-target K562 cells (FIG. 1). NK - target K562 cells are available from the ATCC, Rockville, Md.

Figure 2:
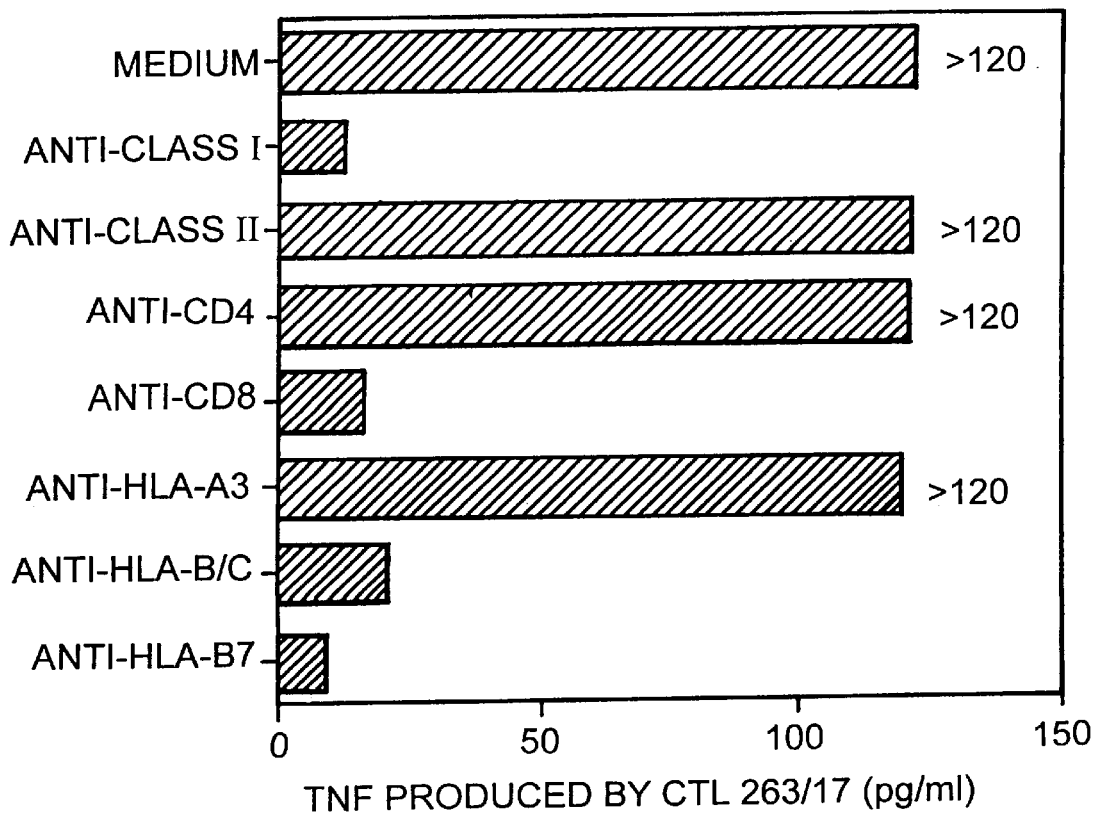
FIG. 2 is a graph depicting the levels of Tumor Necrosis Factor (TNF) produced in the presence of CTL clone 263/17 and various monoclonal antibodies directed against HLA or CD4/CD8 accessory molecules.

CTL clone 263/17 produced TNF when stimulated with the autologous tumor cells. To identify the HLA molecule that presented the antigen to CTL clone 263/17, inhibition experiments were carried out where the production of TNF was tested in the presence of monoclonal antibodies directed against HLA molecules or against CD4/CD8 accessory molecules (FIG. 2). Four monoclonal antibodies were found to inhibit the production of TNF by CTL 263/17:

—monoclonal antibody W6/32, which is directed against all HLA class I molecules (Parham et al., 1979, J. Immunol., 123:342)

—antibody B1.23.2 which recognizes HLA-B and C molecules (Rebai et al., 1983, Tissue Antigens, 22:107)

—antibody ME-1 which specifically recognizes HLA-B7 (Ellis et al., 1982, Hum. Immunol., 5:49)

—antibody B9.4.1 against CD8

No inhibition was found with antibodies directed against HLA Class II DR molecules (L243: Lampson et al., 1980, J. Immunol., 125:293), against HLA-A3 (GAPA 3: Berger et al., 1982 Hybridoma, 1:87) or against CD4 (13B.8.82). The conclusion was that CTL 263/17 was of the CD8 type, and recognized an antigen presented by HLA-B7.

Figure 3:
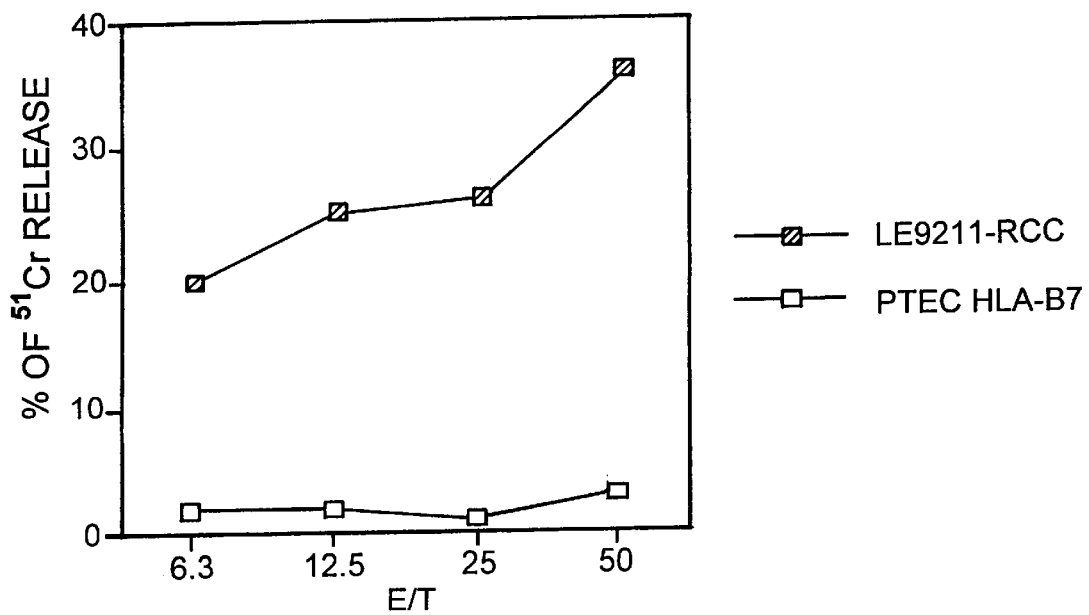
FIG. 3 is a graph depicting the ability of CTL Clone 263/17 to lyse LE 9211-RCC kidney tumor cells vs. the inability to lyse PTEC-HLA-B7 kidney cells from a healthy patient.

To define the tumor specificity of this CTL clone, normal kidney cells derived from another patient which are also HLA-B7 (PTEC-HLA-B7 cells) were tested. These cells derive from the proximal tubular epithelium which is the site of origin of renal cell carcinoma. PTEC-HLA-B7 cells were not lysed by the CTL, suggesting that the antigen is specifically expressed on tumors (FIG. 3).

Figure 4:
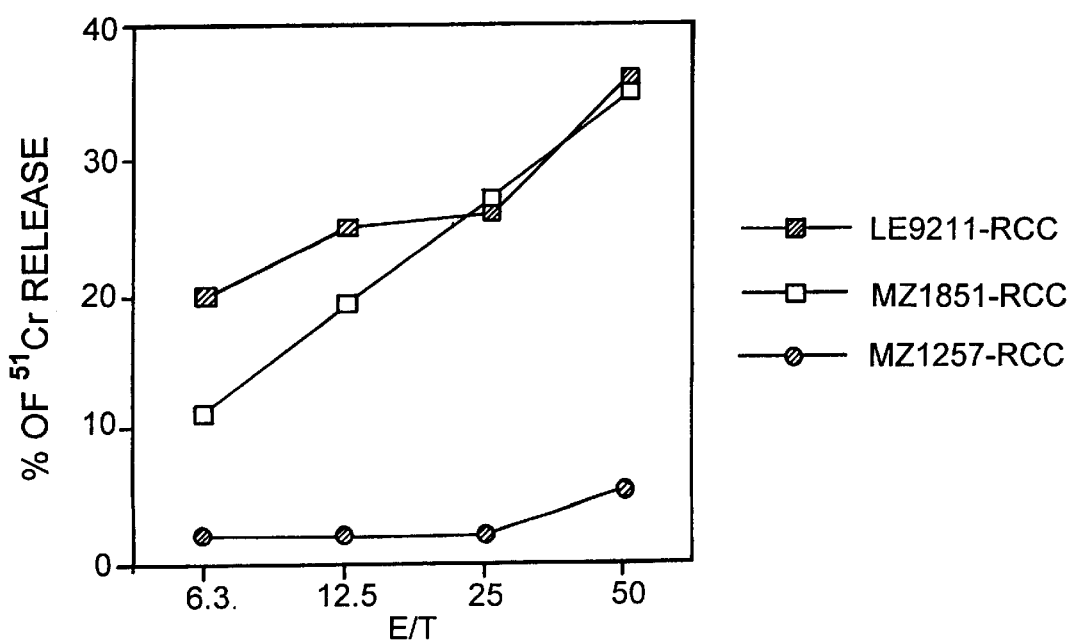
FIG. 4 is a graph showing the ability of CTL Clone 263/17 to lyse renal cell carcinoma line MZ 1851 RCC, which is derived from a different patient, showing that the antigen is shared by independent tumors.

Renal cell carcinoma line MZ-1851, which is derived from another HLA-B7 patient, was also lysed by the CTL, showing that the antigen is shared by independent tumors (FIG. 4).

EXAMPLE 2

Isolation of a cDNA clone that directs the expression of the antigen recognized by CTL 263/17

A. cDNA library

RNA was isolated from LE-9211-RCC, and poly-A+ RNA was purified by oligo-dT binding. cDNA was prepared by reverse transcription with an oligo-dT primer containing a Not I site, followed by second strand synthesis (Superscript Choice System, BRL, Life Technologies). The cDNA was then ligated to a BstX I adaptor, digested with Not I, size-fractionated (SEPHACRYL S-500 HR columns, BRL, Life Technologies) and cloned unidirectionally into the BstX I and Not I sites of pcDNA-I-Amp (Invitrogen). The recombinant plasmid was then electroporated into DH5α E. coli bacteria. 1500 pools of 100 recombinant bacteria were amplified and plasmid DNA of each pool was extracted by alkaline lysis, potassium acetate precipitation and phenol extraction.

B. Transfection of COS cells

Plasmid DNA from the different pools was co-transfected into COS cells with 60 ng of the HLA-B7 cDNA (cloned by PCR from the cDNA of another HLA-B7 patient and inserted into plasmid vector pcDSRalpha). The transfection was made in duplicate wells. Briefly, samples of COS-7 cells were seeded, at 15,000 cells/well into tissue culture flat bottom microwells, in DMEM supplemented with 10% fetal calf serum. The cells were incubated overnight at 37° C., medium was removed and then replaced by 50 μl/well of DMEM medium containing 10% NU-SERUM (Collaborative Research, Bedford, Mass.), 400 μg/ml DEAE-dextran, and 100 μM chloroquine, plus 100 ng of the plasmids. Following four hours of incubation at 37° C., the medium was removed, and replaced by 50 μl of PBS containing 10% dimethyl sulfoxide (DMSO). This medium was removed after two minutes and replaced by 200 μl of DMEM supplemented with 10% FCS.

Following this change in medium, COS cells were incubated for 24–48 hours at 37° C. The transfectants then were screened with CTL 263/17. After first removing the medium, 3000 CTL 263/17 cells were added to each well in 100 μl of medium containing 25 U/ml IL-2. The amount of TNF present in the supernatant was then measured by testing its cytotoxicity for WEHI 164.13 cells. Most pools gave a TNF concentration below 10 pg/ml. Two pools (1157 and 1319) gave higher concentrations in both of the duplicate wells (24 to 37 pg/ml). The bacteria of pool 1319 were cloned and 1200 clones were obtained. Their plasmid DNA was extracted and transfected into COS cells with HLA-B7. The transfectants were screened with CTL 263/17. One cDNA clone (9H3) gave a high TNF production by CTL 263/17. FIG. 5 shows the result obtained when this cDNA (60 ng) was transfected into COS cells with the HLA-B7 cDNA (60 ng) and screened with CTL 263/17.

EXAMPLE 3

Sequence of cDNA 9H3 cDNA clone 9H3 is 1130 bp long. This cDNA was not complete because its size was smaller than that of an mRNA observed on a Northern blot (1.6 kb). The 5' end of the cDNA was cloned by RACE-PCR and the entire sequence was confirmed. This entire sequence is shown as SEQ.ID.NO.1. A comparison with the sequences reported in databanks showed at the 3' end a high homology with a short sequence of 235 bp called "expressed sequence tag", whose function is unknown (I), and at the 5' end a limited homology (75% in a stretch of 95 bases) with the antisense strand of two human endogenous retroviruses called RTVL-H2 and RGH2 (2, 3).

The gene was called RAGE, for Renal tumor AntiGEn.

The sequence contains three open reading frames, one of 288 base pairs encoding a protein of 95 residues, another of 222 base pairs encoding a protein of 73 residues, and another of 123 base pairs encoding a protein of 40 residues (SEQ.ID.NOs.2, 4 and 6, respectively). SEQ.ID.NO.6 codes for the TRAP from which the antigenic peptide reactive with CTL 263/17 (as an HLA-B7 /peptide complex) is derived.

EXAMPLE 4

Identification of Additional RAGE Genes

This example describes the identification of three additional RAGE genes and the determination that only the RAGE gene identified in the above examples, now designated RAGE-1, encodes a RAGE TRA reactive with CTL 263/17.

A probe was prepared from RAGE-1 cDNA (as described in copending application Ser. No. 08/408,015now pending) and used to screen a LE9211-RCC cDNA library for additional RAGE genes. Three cDNAs homologous to RAGE, labeled RAGE-2 (SEQ.ID.NO.11), RAGE-3 (SEQ.ID.NO.12) and RAGE-4 (SEQ.ID.NO.13), were isolated. The RAGE-2, 3 and 4 genes were sequenced by standard methods. Comparison of the nucleotide sequences of these RAGE cDNAs with the RAGE-1 cDNA showed that truncated and novel open reading frames (ORFs) were present in the newly identified RAGE cDNAs. RAGE-2 (SEQ.ID.NO.11), RAGE-3 (SEQ.ID.NO.12) and RAGE-4 (SEQ.ID.NO.13) contained an insert within the sequence corresponding to ORF1 (SEQ.ID.NO.6) of RAGE-1, which insert introduced a stop codon in frame. This prematurely terminated ORF was designated ORF1' (SEQ.ID.NO.14). The same insert in RAGE-2, RAGE-3 AND RAGE-4 contained another start codon from which novel ORFs could be initiated, designated ORF4 (SEQ.ID.NO.16) in RAGE-2 and RAGE-3 and ORF4' (SEQ.ID.NO.18) in RAGE-4. ORF4' differed from ORF4 in that it did not have the same 3' end due to a second insert present in the RAGE-4 cDNA. This second insert in the RAGE-4 cDNA resulted in the substitution of a different 3' end for ORF2. This novel RAGE-4 ORF was designated ORF2' (SEQ.ID.NO.20).

The RAGE-2, RAGE-3 and RAGE-4 cDNAs were cloned into expression plasmids by art-standard procedures and transfected as described with HLA-B7 into COS-7 cells to determine if these cDNAs also encoded the antigen recognized by CTL 263/17. Parallel control experiments with the RAGE cDNA (now referred to as RAGE-1) and with LE9211-RCC cells were also performed.

Figure 6:
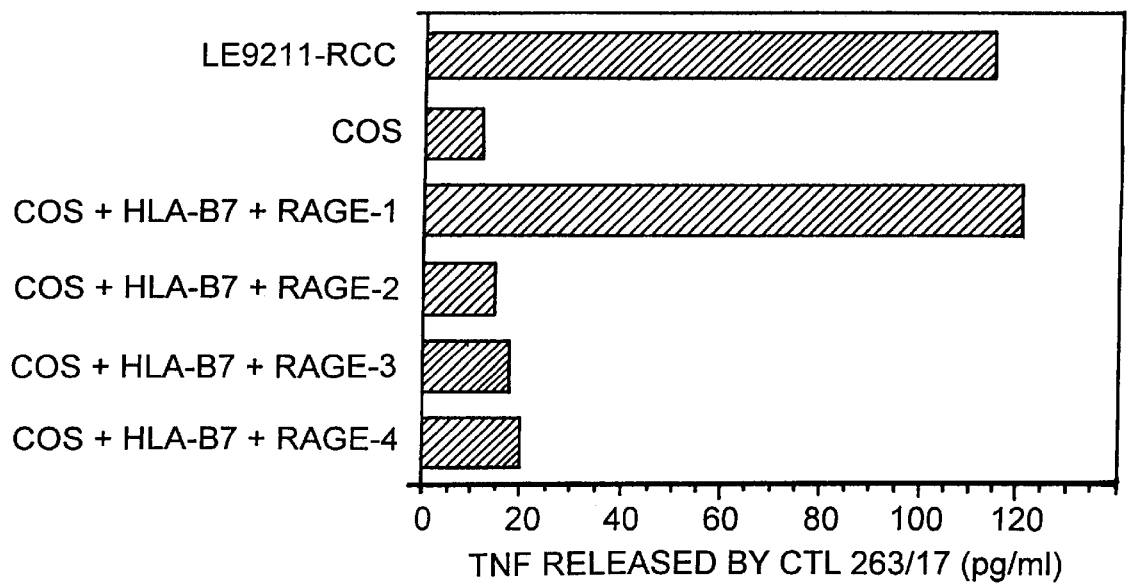
FIG. 6 is a graph depicting the levels of tumor necrosis factor produced when CTL Clone 263/17 is combined with COS cells transfected with HLA-B7 cDNA and a cDNA encoding a TRAP encoded by RAGE-1, RAGE-2, RAGE-3 or RAGE-4.

As shown in FIG. 6, incubation of LE9211-RCC cells or COS-7 cells cotransfected with RAGE-1 and HLA-B7 with CTL 263/17 strongly induced release of TNF by CTL 263/17. Transfection of RAGE-2, RAGE-3 or RAGE-4 did not elicit TNF release. Therefore, only RAGE-1 was able to transfer expression of the antigen recognized by CTL 263/17.

EXAMPLE 5

Identification of ORF containing RAGE tumor rejection antigen

Figure 7:
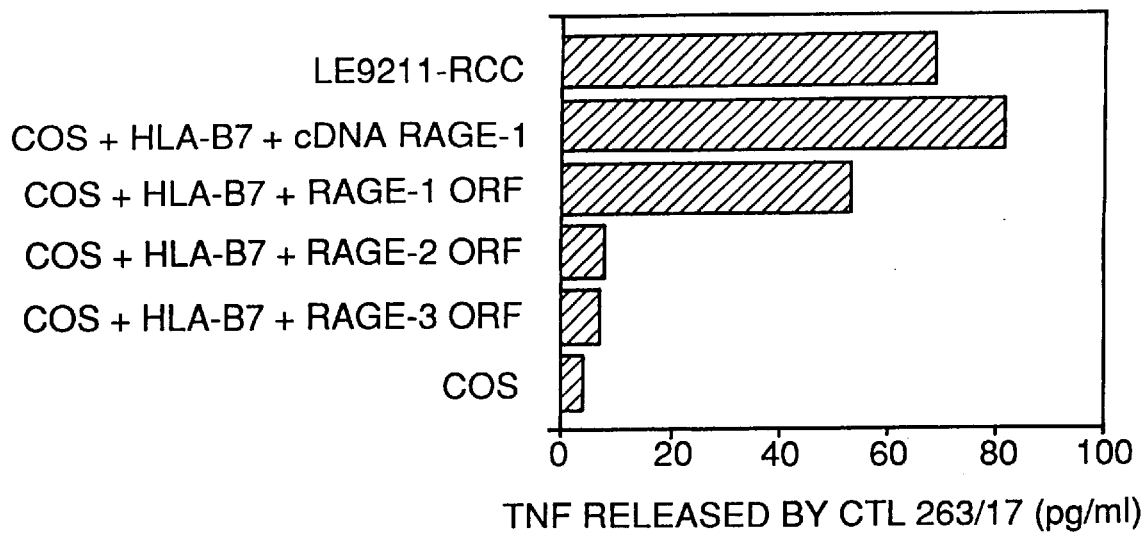
FIG. 7 is a graph showing the levels of tumor necrosis factor produced when CTL Clone 263/17 is combined with COS cells transfected with HLA-B7 cDNA and a cDNA encoding a RAGE TRAP or a minigene encoding ORF1 of a RAGE TRAP.

It was reasoned that the antigenic peptide recognized by CTL 263/17 was encoded by the 3' end of ORF1, since the other ORFs of RAGE-1 were common to RAGE-1, 2, and 3. To test this hypothesis, the DNA sequences corresponding to ORF1 of RAGE 1 and ORF1' of RAGE-2 and RAGE-3 were cloned into an expression vector and transfected into COS-7 cells with HLA-B7 as described above. As positive controls, the RAGE-1 cDNA was cotransfected with HLA-B7 into COS-7 cells or LE2911-RCC cells were used. These transfectants or LE2911-RCC cells were used to provoke release of TNF from CTL 263/17 cells. Among the ORF transfectants, only the ORF1 from RAGE-1 successfully stimulated TNF release from CTL 263/17 cells (FIG. 7). This experiment confirmed that the RAGE antigenic peptide recognized by CTL 263/17 cells was encoded by the 3' end of ORF1 of RAGE-1.

EXAMPLE 6

Identification of RAGE tumor rejection antigen peptide

Synthetic peptides corresponding to the 3' end of RAGE-1 ORF1 were synthesized and tested for stimulation of TNF release from CTL 263/17 cells. COS-7 cells were transfected with HLA-B7 as described above and a synthetic peptide corresponding to a 3' portion of ORF1 was added to the culture. CTL 263/17 cells were added and the production of TNF was measured after 18 hours (FIG. 8). Peptide SPSS-NRIRNTST (SEQ.ID.NO.22) efficiently stimulated the release of TNF from CTL 263/17. Since peptides presented by HLA class I molecules are usually 9 amino acids in length, we tested nonameric peptides (SEQ.ID.NOs. 23, 24 and 25) derived from the dodecameric peptide (SEQ.ID.NO.22) previously used to stimulate TNF release from CTL 263/17 cells. The results of these experiments are shown in FIG. 8. One of these peptides (SPSSNRIRN, SEQ.ID.NO.23) was recognized by CTL 263/17, but to a far lesser extent than the dodecameric peptide, which suggested that the nonamer (SEQ.ID.NO.23) was not the optimal peptide. The decameric peptide (SPSSNRIRNT, SEQ.ID.NO.26) was very efficiently recognized by CTL 263/17.

EXAMPLE 7

Activity of RAGE tumor rejection antigen nonamer and decamer peptides

This example shows the ability of the RAGE TRA peptide to induce lysis of HLA-B7-expressing cells and the relative efficiencies of the nonamer and decamer peptides.

Figure 9:
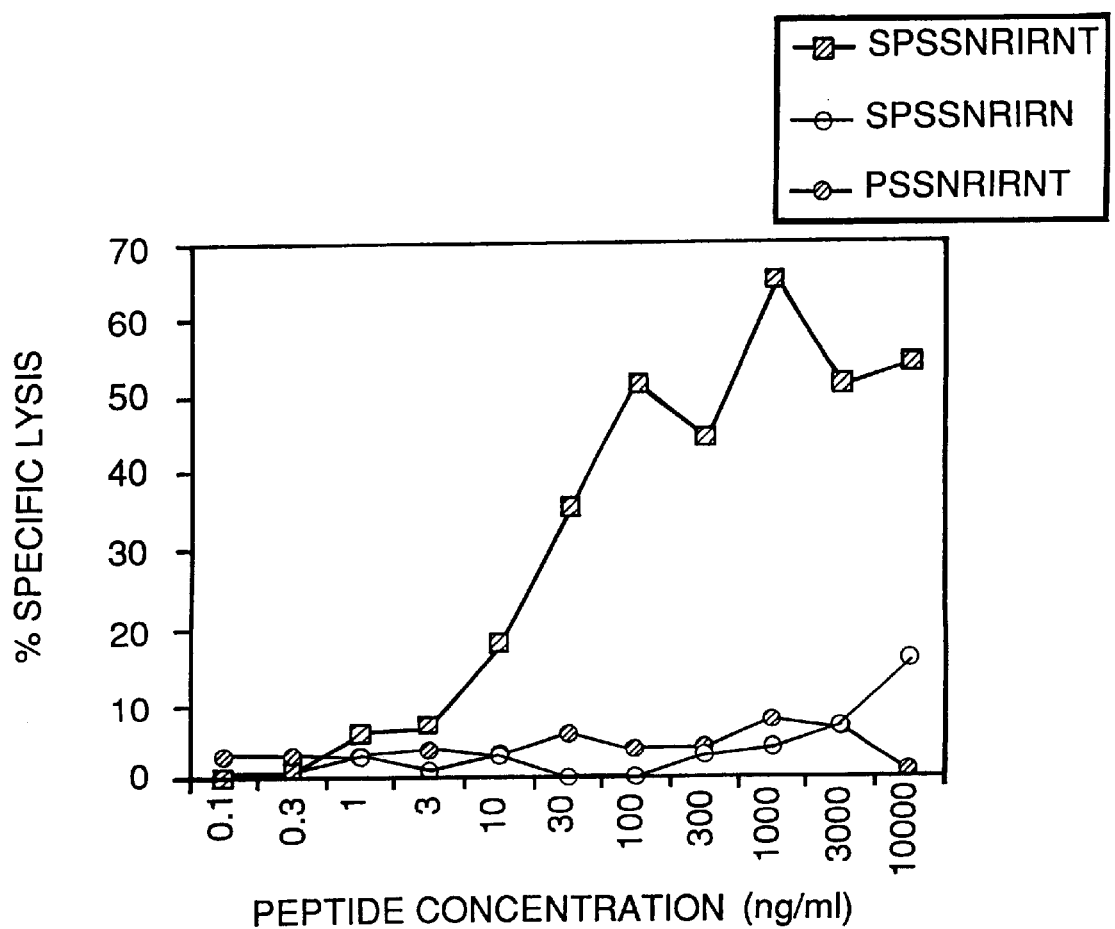
FIG. 9 is a graph depicting the lytic activity of CTL clone 267/13 against HLA-B7+ LB23-EBV B cells pulsed with increasing concentrations of the peptides including a RAGE TRA (SPSSNRIRNT, SEQ ID NO:26; SPSSNRIRN, SEQ ID NO:23; PSSNRIRNT, SEQ ID NO:24).

Nonameric and decameric RAGE peptides (SEQ.ID.NOs. 23 and 26, respectively) were tested for the ability to induce cell lysis of HLA-B7$^+$ LB23-EBV B cells by CTL 263/17 cells in a dose response assay. Lyophilized peptides were dissolved at 20 mg/ml in DMSO, then diluted to 2 mg/ml in 10 mM acetic acid and stored at −80° C. Target cells, HLA-B7$^+$ EBV-transformed lymphoblastoid cells (LB23-EBV cells), were labeled with $^{51}$Cr, as described above, for 1 hour at 37° C. followed by extensive washing to remove unincorporated label. LB23-EBV cells were then incubated in 96-well microplates in the presence of various concentrations of peptides for 30 minutes at 37° C. CTL263/17 were then added in an equal volume of medium at an effector:target ratio of 10:1. Chromium-51 release was measured after 4 hours. FIG. 9 shows the results of the dose response assay. Half maximal lysis of LB23-EBV cells was induced at a concentration of 30 ng/ml SPSSNRIRNT peptide (SEQ.ID.NO.26).

EXAMPLE 8

Expression of RAGE-1 gene

The expression of RAGE was tested by PCR using the following primers:

SEQ.ID.NO.8

—GTG TCT CCT TCG TCT CTA CTA (sense primer, nucleotide position 209–229)

SEQ.ID.NO.9

—GGT GTG CCG ATG ACA TCG (antisense primer common to all RAGE genes, nucleotide position 385–402)

SEQ.ID.NO.10

—GAG GTA TTC CTG ATC CTG (antisense primer specific for RAGE-1, nucleotide position 431–448)

First, total RNA was taken from the particular sample, using art recognized techniques. This RNA was used to prepare cDNA. The protocol used to make the cDNA involved combining 4 µl of 5×reverse transcriptase buffer, 1 µl of each dNTP (10 mM), 2 µl of dithiothreitol (100 mM), 2 µl of dT-15 primer (20 µM), 0.5 µl of RNasin (40 units/µl), and 1 µl of M-MLV reverse transcriptase (200 units/µl). Next, 6.5 µl of template RNA (1 µg/3.25 µl water, or 2 µg total template RNA) was added. The total volume of the mixture was 20 µl. This was mixed and incubated at 42° C. for 60 minutes, after which it was chilled on ice. A total of 80 µl of water was then added, to 100 µl total. This mixture was stored at −20° C. until used in PCR.

The reagents for PCR included:

—5 microliters of 10× DYNAZYME buffer

—20 pmoles of each primer

—5 nanomoles of each dNTP

—1 unit of polymerizing enzyme "DYNAZYME" (2 units/µl)

—5 µl of cDNA (corresponding to 100 ng total RNA)

—water to a final volume of 50 µl

The mixture was combined, and layered with one drop of mineral oil. The mixture was transferred to a thermocycler block, preheated to 94° C., and amplification was carried out for one cycle of 15 min at 94° C., followed by 33 cycles of:

—1 min. at 94° C.

—2 min. at 56° C. or 60° C. (see below)

—3 min. at 72° C. A final extension step of 15 min. was then performed at 72° C. Expression of all RAGE genes was tested by PCR amplification with pan-RAGE sense (SEQ.ID.NO.8) and antisense (SEQ.ID.NO.9) primers using an annealing step of 60° C. for 2 minutes. Expression of only RAGE-1 gene was tested by PCR amplification with pan-RAGE sense (SEQ.ID.NO.8) and RAGE-1-specific antisense (SEQ.ID.NO.10) primers using an annealing step of 56° C. for 2 minutes. The PCR product of 194 base pairs (general to all RAGE genes tested) and 239 base pairs (specific for RAGE-1 genes) were visualized on an agarose gel (1.5%) containing ethidium bromide.

The gene was found to be tumor-specific. The gene was silent in all normal tissues tested, except for retina. In particular, the gene was silent in adrenals, bladder, bone marrow, brain, breast, cerebellum, colon, heart, kidney, liver, lung, nevus, ovary, placenta, skin, testis, uterus. The gene, however, was found to be expressed in a variety of tumor cell lines and tumor tissue samples (Table 1). It is also expressed in some other tumors which are not listed here, although not frequently.

TABLE 1

Expression of RAGE-1 Gene in Tumor Samples

| | Number of Tumors Expressing | |
|---|---|---|
| Histological Type | ALL RAGE | RAGE-1 |
| Tumor Samples | | |
| Renal carcinoma | 1/54 | 1/54 |
| Sarcomas | 4/21 | 3/21 |
| Bladder tumors | superficial - 0/30 | 0/30 |
| | infiltrating - 3/32 | 3/32 |
| Melanomas | primary lesions - 1/48 | 1/48 |
| | metastases - 6/123 | 6/123 |
| Head and neck tumors | 1/43 | 1/43 |
| Mammary carcinomas | 3/130 | 1/130 |
| Prostatic carcinomas | 0/7 | 0/7 |
| Colorectal carcinomas | 0/40 | 0/40 |
| Leukemias and Lymphomas | 0/18 | 0/18 |
| Lung carcinomas (NSCLC[1]) | 0/43 | 0/43 |
| Mesotheliomas | 1/2 | 0/2 |
| Tumor Cell Lines | | |
| Renal carcinoma | 7/17 | 6/17 |
| Bladder tumors | 3/3 | 3/3 |
| Mesotheliomas | 8/16 | 6/16 |
| Head and neck tumors | 2/6 | 1/6 |
| Sarcomas | 1/3 | 1/3 |
| Melanomas | 10/71 | 6/71 |
| Colorectal carcinomas | 1/16 | 1/16 |
| Lung carcinomas (NSCLC[1]) | 0/2 | 0/2 |
| Leukemias and Lymphomas | 0/11 | 0/11 |

[1]NSCLC: non-small cell lung carcinoma.

The foregoing examples show the isolation of a nucleic acid molecule which codes for a TRAP. This TRAP coding molecule, however, is not homologous with any of the previously disclosed coding sequences described in the references set forth supra. Hence, one aspect of the invention is an isolated nucleic acid molecule which includes all or a unique portion of the nucleotide sequence set forth in SEQ.ID.NO.1, SEQ.ID.NO.2, SEQ.ID.NO.4 or SEQ.ID.NO.6. It is also expected that antigens derived from other RAGE ORFs encoded by SEQ.ID.NOs. 11, 12 and 13 may be recognized cytolytic T lymphocyte clones other than CTL263/17. Thus, the invention in another aspect involves any one or more of the RAGE family of genes, including isolated unique portions thereof such as portions encoding TRAPs and TRAs, RAGE TRAPs and TRAs derived therefrom and all of the diagnostic and therapeutic modeleties relating thereto. The foregoing sequences are not MAGE, BAGE or GAGE sequences, as will be seen by comparing them to the MAGE, BAGE or GAGE sequences described in the references.

Also a part of the invention are those nucleic acid sequences which also code for a non-MAGE, non-BAGE and non-GAGE tumor rejection antigen precursor but which hybridize to a nucleic acid molecule consisting of the above described nucleotide sequences, under stringent conditions. The term "stringent conditions" as used herein refers to parameters with which the art is familiar. More specifically, stringent conditions, as used herein, refers to hybridization at 65° C. in hybridization buffer (3.5×SSC, 0.02% FICOOL (a synthetic polymer of sucrose) 0.02% Polyvinyl pyrolidone, 0.02% Bovine Serum Albumin, 25 mM $NaH_2PO_4$ (pH7), 0.5% SDS, 2mM EDTA). SSC is 0.15M Sodium Chloride/0.15M Sodium Citrate, pH 7; SDS is Sodium dodecyl Sulphate; and EDTA is Ethylene diamine tetra acetic acid. After hybridization, the membrane upon which the DNA is transferred is washed at 2×SSC at room temperature and then at 0.1×SSC/0.1×SDS at 65° C.

There are other conditions, reagents, and so forth which can be used, which result in the same degree of stringency. The skilled artisan will be familiar with such conditions, and thus they are not given here. The skilled artisan also is familiar with the methodology for screening cells, preferably cancer cells, for expression of such molecules which then are routinely isolated, followed by isolation of the pertinent nucleic acid.

In screening for RAGE family members, a Southern blot may be performed using the foregoing conditions, together with a $^{32}P$ probe. After washing the membrane to which the DNA was finally transferred, the membrane can be placed against X-ray film to detect the radioactive signal.

The invention thus provides isolated unique fragments of SEQ.ID.NO.1 or its complement. A unique fragment is one that is a 'signature' for SEQ.ID.NO.1 and related RAGE genes. It, for example, is long enough to assure that its precise sequence is not found in molecules outside of the RAGE family as defined by claim 1. Preferred unique fragments are those found only in ORF1 or its complement. Unique fragments can be used as probes in Southern blot assays to identify RAGE family members including those expressing ORF1 or can be used in amplification assays such as those employing PCR. As known to those skilled in the art, large probes such as 200 bp or more are preferred for certain uses such as Southern blots, while smaller fragments will be preferred for uses such as PCR. As will be recognized by those skilled in the art, the size of a unique fragment will depend upon its conservency in the genetic code. Thus, some regions of SEQ.ID.NO.1 will require longer segments to be unique while others will require only short segments, typically between 12 and 32 bp. Virtually any segment of SEQ.ID.NO.1 that is 18 or more nucleotides in length will be unique. Those skilled in the art are well versed in methods for selecting such sequences, typically on the basis of the ability of the unique fragment to selectively distinguish the sequence of interest from nonfamily members. A comparison of the sequence of the fragment to those on known data bases typically is all that is necessary, although in vitro confirmatory hybridization and sequencing analysis may be performed.

For any pair of PCR primers constructed and arranged to selectively amplify RAGE-1, a RAGE-1 specific primer may be used. Such a primer is a contiguous stretch of RAGE-1 which hybridizes to both sides of the insertion point in ORF1 which is altered by the insertion of additional nucleotides in other RAGE genes. Such a specific primer would fully hybridize to a contiguous stretch of nucleotides only in RAGE-1, but would hybridize only in part to RAGE genes that do not share ORF1. For efficient PCR priming and RAGE 1 identification, the RAGE 1 specific primer should be constructed and arranged so it does not hybridize efficiently at its 3' end to RAGE genes other than RAGE 1. To accomplish this, the primer can be described as having two ends: a 5' end that is contiguous with and complementary to one side of the insertion point joined directly to a 3' end that is contiguous with and complementary to the opposite side of the insertion point. By making the 5' end of the primer substantially longer than the 3' end, and by making the 3' end short (i.e. 1–4 nucleotides), then the kinetics of hybridization will strongly favor hybridization at the 5' end. In this instance, 3' initiated PCR extension will occur only when both the 5' and 3' ends hybridize to the nucleic acid, i.e. only when ORF1 is present without an insert.

RAGE-1 specific primers, as described above, may be designed to prime DNA synthesis on either strand of the DNA helix, described herein as the Watson or the Crick strands. The sequence in RAGE 1 which flanks the insertion point, is 5'-CAAACANGGATCA-3' (SEQ.ID.NO.29; Watson strand, N is a nucleotide insert). A RAGE-1 specific primer designed to preferentially amplify the Watson strand of RAGE-1 typically would comprise 12 and preferably 15 or more nucleotides complimentary to the nucleotides of the Watson strand 3' to the insertion point. The remaining portion of the primer would be one to four nucleotides long and would be complimentary to the sequence 5' to the insertion point. Such a primer would be perfectly complimentary and contiguous with its compliment in RAGE-1. The 3' end of the primer would hybridize to its compliment in the Watson strand and initiate extension. In RAGE genes other than RAGE-1, the insertion of noncomplementary nucleotides at the insertion point of ORF1 would substantially eliminate hybridization of the 3' end of the RAGE-1 specific primer to the Watson strand 5' of the insert. The mismatch generated at the 3' end of the primer when hybridized to RAGE genes, other than RAGE-1, would preclude efficient amplification of those genes. Exemplary primers consist essentially of the following sequences, wherein N is zero, one or more contiguous nucleotides on the appropriate Watson or Crick strands:

5'-NTATTCCTGATCCT-3'(SEQ.ID.NO.30);
5'-NTATTCCTGATCCTG-3'(SEQ.ID.NO.31);
5'-NTATTCCTGATCCTGT-3'(SEQ.ID.NO.32);
5'-NTATTCCTGATCCTGTT-3'(SEQ.ID.NO.33);
5'-NCAAGTTCAAACAG-3'(SEQ.ID.NO.34);
5'-NCAAGTTCAAACAGG-3'(SEQ.ID.NO.35);
5'-NCAAGTTCAAACAGGA-3'(SEQ.ID.NO.36); and
5'-NCAAGTTCAAACAGGAT-3'(SEQ.ID.NO.37).

The expression of RAGE-1 may also be detected by PCR using primers which initiate extension on opposite sides of the insertion point. Analysis of amplification products can distinguish RAGE-1 amplification products from nonRAGE-1 amplification products by the length of the amplification products. Because the RAGE-1 gene does not contain the insert present in other RAGE genes, amplification products derived from RAGE-1 will be shorter than amplification products derived from other RAGE genes (by about 37 base pairs). This difference may be distinguished readily using standard methods in the art. Additional methods which can distinguish nucleotide sequences of substantial homology, such as ligase chain rection ("LCR") and other methods, will be apparent to skilled artisans.

The invention also includes the use of nucleic acid sequences which include alternative codons that encode the same amino acid residues as encoded by SEQ.ID.NO.1. For example, as disclosed above in Example 7, a decameric peptide SPSSNRIRNT (SEQ.ID.NO.26) is a RAGE tumor rejection antigen. The serine residues (amino acids No. 1, 3 and 4 of SEQ.ID.NO.23) for example, are encoded by the codons TCA, AGT and TCA, respectively. In addition to TCA and AGT, serine amino acid residues may also be encoded by the codons TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues comprising a RAGE tumor rejection antigen include: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences.

The examples above also show the isolation of peptides which are RAGE TRAs. These peptides are processed translation products of the nucleic acids of SEQ.ID.NO.1. As such, it will be appreciated by one of ordinary skill in the art that the translation products from which a RAGE TRA is processed to a final form for presentation by HLA-B7 may be of any length or sequence so long as they encompass the RAGE TRA. As demonstrated in the examples above, peptides or proteins as small as 9, 10, or 12 amino acids and as large as the amino acid sequence encoded by ORF1 are appropriately processed, presented by HLA-B7 and recognized by CTL263/17. The peptide of SEQ.ID.NO.23 may have one, two, three, four, five, six, seven, eight, nine, ten, or more amino acids added to either or both ends. The antigenic portion of such a peptide is cleaved out under physiological conditions for presentation by HLA class I molecules.

The amino acid sequence of proteins and peptides from which RAGE TRAs are derived may be of natural or non-natural origin, that is, they may comprise a natural RAGE TRAP molecule or may comprise a modified sequence as long as the amino acid sequence retains the tumor rejection antigen sequence recognized by CTL 263/17 when presented on the surface of a cell by HLA-B7. For example, RAGE tumor rejection antigens in this context may be fusion proteins of a RAGE tumor rejection antigen and unrelated amino acid sequences, the translated polypeptide of ORF1 of the RAGE-1 gene, synthetic peptides of amino acid sequences shown in SEQ.ID.NOs.22, 23 and 26, labeled peptides, peptides isolated from patients with renal cell carcinoma, peptides isolated from cultured cells which express RAGE-1, peptides coupled to nonpeptide molecules for example in certain drug delivery systems and other molecules which include the amino acid sequence of SEQ.ID.NO.23.

It will also be seen from the examples that the invention embraces the use of the sequences in expression vectors, as well as to transfect host cells and cell lines, be these prokaryotic (e.g., E. coli), or eukaryotic (e.g., CHO cells, COS cells, yeast expression systems and recombinant baculovirus expression in insect cells). The expression vectors require that the pertinent sequence, i.e., those described supra, be operably linked to a promoter. As it has been found that human HLA-B7 presents a TRA derived from these genes, the expression vector may also include a nucleic acid sequence coding for HLA-B7. In a situation where the vector contains both coding sequences, it can be used to transfect a cell which does not normally express either one. The TRAP or TRA coding sequence may be used alone, when, e.g. the host cell already expresses HLA-B7. Of course, there is no limit on the particular host cell which can be used. As the vectors which contain the two coding sequences may be used in HLA-B7 presenting cells if desired, and the nucleic acid coding for the TRAP or TRA can be used in host cells which do not express HLA-B7.

The invention also embraces so-called expression kits, which allow the artisan to prepare a desired expression vector or vectors. Such expression kits include at least separate portions of at least two of the previously discussed materials. Other components may be added, as desired.

To distinguish the nucleic acid molecules and the TRAPs of the invention from the previously described MAGE family, BAGE gene and GAGE gene, the invention shall be referred to as the RAGE family of genes and TRAPs. Hence, whenever "RAGE" is used herein, specifically excluded are MAGE, BAGE and GAGE genes, gene products, TRAPs and TRAs.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-B7. In the former situation, such determinations can be carried out via any standard nucleic acid determination assay, including the polymerase chain reaction, or assaying with labeled hybridization probes. In the latter situation, assaying with binding partners for complexes of TRA and HLA, such as antibodies, is especially preferred. An alternate method for determination is a TNF release assay, of the type described supra.

The isolation of the TRAP gene also makes it possible to isolate the TRAP molecule itself, and/or TRAs derived therefrom, especially TRAP and/or TRA molecules containing the amino acid sequences coded for by SEQ.ID.NO.1 or 6. Other TRAPs or TRAs encoded by SEQ.ID.NOs. 1, 11, 12 and 13 and recognized by other CTL clones and/or presented by other HLA molecules may be isolated by the procedures detailed herein. (There are numerous HLA molecules known to those skilled in the art, including but not limited to, those encoded by HLA-A, HLA-B, HLA-C, HLA-E, HLA-F and HLA-G genes.) A variety of methodologies well-known to the skilled practitioner can be utilized to obtain isolated TRAP molecules, and/or TRAs derived therefrom. The protein may be purified from cells which naturally produce the protein. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce protein. Peptides comprising TRAs of the invention may also be synthesized in vitro. Those skilled in the art also can readily follow known methods for isolating proteins in order to obtain isolated TRAP and/or TRAs derived therefrom. These include, but are not limited to, immunochromotography, HPLC, size-exclusion chromatography, ion-exchange chromatography and immune-affinity chromatography. These isolated molecules when processed and presented as the TRA, or as complexes of TRA and HLA, such as HLA-B7, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection. Vaccines also encompass naked DNA or RNA, encoding a RAGE TRA or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (Science 259:1745–1748, 1993).

The TRAP molecule, its associated TRAs, as well as complexes of TRA and HLA, may be used to produce antibodies, using standard techniques well known to the art. Standard reference works setting forth the general principles of antibody production include Catty, D., *Antibodies, A Practical Approach,* Vol. 1, IRL Press, Washington DC (1988); Klein, J., *Immunology: The Science of Cell-Non-Cell Discrimination,* John Wiley and Sons, New York (1982); Kennett, R., et al., *Monoclonal Antibodies, Hybridoma, A New Dimension In Biological Analyses,* Plenum Press, New York (1980); Campbell, A., *Monoclonal Antibody Technology,* in *Laboratory Techniques and Biochemistry and Molecular Biology,* Vol. 13 (Burdon, R. et al. EDS.), Elsevier Amsterdam (1984); and Eisen, H. N., *Microbiology,* third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the TRA/HLA complexes described herein.

When "disorder" is used herein, it refers to any pathological condition where the tumor rejection antigen precursor is expressed. An example of such a disorder is cancer, renal cell carcinoma in particular.

Therapeutic approaches based upon the disclosure are premised on a response by a subject's immune system, leading to lysis of TRA presenting cells, such as HLA-B7 cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant, such as a COS cell of the type described supra. These transfectants present the desired complex of their surface and, when combined with a CTL of interest, stimulate its proliferation. COS cells, such as those used herein are widely available, as are other suitable host cells. Specific production of a CTL clone has been described above. The clonally expanded autologous CTLs then are administered to the subject. Other CTLs specific to RAGE-1 and CTLs specific to RAGE TRAs encoded by RAGE-2, 3, or 4 may be isolated and administered by similar methods.

To detail a therapeutic methodology, referred to as adoptive transfer (Greenberg, J. Immunol. 136(5): 1917 (1986); Riddel et al., Science 257: 238 (Jul 10, 1992); Lynch et al, Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a RAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a RAGE derived, TRA is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated tumor cells or cells transfected with one or both of the genes necessary for presentation of the complex. Chen et at., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. For example, nucleic acids which encode a RAGE TRA may be operably linked to promoter and enhancer sequences which direct expresion of the RAGE TRA in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding RAGE TRAs. Nucleic acids encoding a RAGE TRA also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials de facto "infect" host cells. The cells which result present the complex of interest, and are recognized by autologous CTLs, which then proliferate.

A similar effect can be achieved by combining the TRAP or a stimulatory fragment thereof with an adjuvant to facilitate incorporation into HLA-B7 presenting cells in vivo. The TRAP is processed to yield the peptide partner of the HLA molecule while the TRA is presented without the need for further processing. Generally, subjects can receive an intradermal injection of an effective amount of the RAGE TRAP, and/or TRAs derived therefrom. Initial doses can be followed by booster doses, following immunization protocols standard in the art.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (Science 268: 1432–1434, 1995).

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. This can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 miligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

REFERENCES

1) Gleser, L., and Swaroop, A. 1992. Expressed sequence tags and chromosomal localization of cDNA clones from a subtracted retinal pigment epithelium library. Genomics 13, 873–876.
2) Mager, D., and Freeman, J. D. 1987. Human endogenous retrovirus-like genome with Type C pol sequences and gag sequences related to human T-cell lymphotropic viruses. J. Virol. 61, 4060–4066.
3) Hirose, Y., Takamatsu, M., Harada, F. 1993. Presence of env genes in members of the RTVL-H family of human endogenous retrovirus-like elements. Virology 192, 52–61.

We claim:

1. An isolated polypeptide comprising the amino acid sequence of SEQ.ID.NO.23.

2. The isolated polypeptide of claim 1 wherein the isolated polypeptide comprises the amino acid sequence of SEQ.ID.NO.26.

3. The isolated polypeptide of claim 1 wherein the isolated polypeptide consists of an amino acid sequence selected from the group consisting of SEQ.ID.NO.23 and SEQ.ID.NO.26.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
       (A) LENGTH: 1311 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (vi) ORIGINAL SOURCE:
       (A) ORGANISM: Homo sapiens (xi) SEQUENCE DESCRIPTION: SEQ ID NO:1:

```
GGTGAGCAGC CAAAGCAGGC ATCCCCGCAG TTGACTTGCC ACCAAGGGAA TGTGGGTGAA      60

TGACCAAGGC AGGCATCCTC GCGGTGATCA GACACCAATG GAGTGTGGGT GAATAATCAG     120

GCAGGCATCC CCGCAGTGAT TAAACACCAA GAGAAGACTA TTCCTGAGTC TGTGACTGGT     180

GCTGGAGTTT TGAGTCCACA GATAAAATGT GTCTCCTTCG TCTCTACTAG AGAGGAAAAA     240

GAACTGGAAT TGGAAGAACA GGGAGACTGA AGGGTAGCAA GAGAGGCTGG AGAAGAGAGT     300

GAAAAGACCG CTTACCTGAT TTGAAATTGT CTGCAGCCCC TCTTTCCTGG AGTAAATGAA     360

CTGGACCAAA TCTCAAAAAA TCCACGATGT CATCGGCACA CCCGCTCAGA AGATCCTCAC     420

CAAGTTCAAA CAGGATCAGG AATACCTCTA CTAACAACCA ATTTGTCCCC ACAATGCCTC     480

TCCCTCCTGC ACGCAATGGT GGCCTATGAT CCCGATGAGA GAATCGCCGC CCACCAGGCC     540

CTGCAGCACC CCTACTTCCA AGAACAGAGA AACAGTCCCT AAAGCAAGAG GAGGACCGTC     600

CCAAGAGACG AGGACCGGCC TATGTCATGG AACTGCCCAA ACTAAAGCTT TCGGGAGTGG     660

TCAGACTGTC GTCTTACTCC AGCCCCACGC TGCAGTCCGT GCTTGGATCT GGAACAAATG     720

GAAGAGTGCC GGTGCTGAGA CCCTTGAAGT GCATCCCTGC GAGCAAGAAG ACAGATCCGC     780

AGAAGGACCT TAAGCCTGCC CCGCAGCAGT GTCGCCTGCC CACCATAGTG CGGAAAGGCG     840

GAAGATAACT GAGCAGCACC GTCGTCTCGA CTTCGGAGGC AACACCAAGC CCGACCGGGC     900

CAGGCCTGGG TGATCTGCTG CTGAGACGCC ACGGAGGGCT GGGGATGCGC CTGCGTCCGT     960

TTCGCGCTGG CCGGGCTCT GGGTGCTGCC CTGCGCCCTG CCGCACCCGC GGCCCGCGCA    1020

GCTGCCTAGG ATGTTCTGGG CTAATATACT TGTAAAACCA CCGCATTCTA GGGTTTTCTT    1080

TCATTTTCGT TAAGAATTTG GGGCAGGAAA TACTTTGTAA CTTTGTATAT GAATCAAAAC    1140

AAACGAGCAG GCATTTCTGT GATGTGTTGG GCGTGGTTGG AAGGTGGGTT CTGCGTGTCC    1200

CTTCCCAGCG CTGCTGGTCA GTCGTGGAGC GCCATCATGT CTTACCAGTG ACGCTGCTGA    1260

CACCCCTGAC TTTTATTAAA GAATAAGCTG TCGTTAAAAA AAAAAAAAA A              1311
```

(2) INFORMATION FOR SEQ ID NO:2:

(i) SEQUENCE CHARACTERISTICS:
       (A) LENGTH: 288 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (v) FRAGMENT TYPE: internal (vi) ORIGINAL SOURCE:
       (A) ORGANISM: Homo sapiens (ix) FEATURE:
       (A) NAME/KEY: CDS
       (B) LOCATION: 1..288

(xi) SEQUENCE DESCRIPTION: SEQ ID NO:2:

```
ATG ATC CCG ATG AGA GAA TCG CCG CCC ACC AGG CCC TGC AGC ACC CCT      48
Met Ile Pro Met Arg Glu Ser Pro Pro Thr Arg Pro Cys Ser Thr Pro
 1               5                  10                  15

ACT TCC AAG AAC AGA GAA ACA GTC CCT AAA GCA AGA GGA GGA CCG TCC      96
Thr Ser Lys Asn Arg Glu Thr Val Pro Lys Ala Arg Gly Gly Pro Ser
             20                  25                  30

CAA GAG ACG AGG ACC GGC CTA TGT CAT GGA ACT GCC CAA ACT AAA GCT     144
Gln Glu Thr Arg Thr Gly Leu Cys His Gly Thr Ala Gln Thr Lys Ala
         35                  40                  45

TTC GGG AGT GGT CAG ACT GTC GTC TTA CTC CAG CCC CAC GCT GCA GTC     192
Phe Gly Ser Gly Gln Thr Val Val Leu Leu Gln Pro His Ala Ala Val
     50                  55                  60

CGT GCT TGG ATC TGG AAC AAA TGG AAG AGT GCC GGT GCT GAG ACC CTT     240
Arg Ala Trp Ile Trp Asn Lys Trp Lys Ser Ala Gly Ala Glu Thr Leu
 65                  70                  75                  80

GAA GTG CAT CCC TGC GAG CAA GAA GAC AGA TCC GCA GAA GGA CCT TAA     288
Glu Val His Pro Cys Glu Gln Glu Asp Arg Ser Ala Glu Gly Pro
                 85                  90                  95
```

(2) INFORMATION FOR SEQ ID NO:3:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ile Pro Met Arg Glu Ser Pro Pro Thr Arg Pro Cys Ser Thr Pro
 1               5                  10                  15

Thr Ser Lys Asn Arg Glu Thr Val Pro Lys Ala Arg Gly Gly Pro Ser
             20                  25                  30

Gln Glu Thr Arg Thr Gly Leu Cys His Gly Thr Ala Gln Thr Lys Ala
         35                  40                  45

Phe Gly Ser Gly Gln Thr Val Val Leu Leu Gln Pro His Ala Ala Val
     50                  55                  60

Arg Ala Trp Ile Trp Asn Lys Trp Lys Ser Ala Gly Ala Glu Thr Leu
 65                  70                  75                  80

Glu Val His Pro Cys Glu Gln Glu Asp Arg Ser Ala Glu Gly Pro
                 85                  90                  95
```

(2) INFORMATION FOR SEQ ID NO:4:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (v) FRAGMENT TYPE: internal (vi) ORIGINAL SOURCE:
            (A) ORGANISM: Homo sapiens (ix) FEATURE:
            (A) NAME/KEY: CDS
            (B) LOCATION: 1..222

(xi) SEQUENCE DESCRIPTION: SEQ ID NO:4:

```
ATG GAA CTG CCC AAA CTA AAG CTT TCG GGA GTG GTC AGA CTG TCG TCT      48
Met Glu Leu Pro Lys Leu Lys Leu Ser Gly Val Val Arg Leu Ser Ser
 1               5                  10                  15

TAC TCC AGC CCC ACG CTG CAG TCC GTG CTT GGA TCT GGA ACA AAT GGA      96
Tyr Ser Ser Pro Thr Leu Gln Ser Val Leu Gly Ser Gly Thr Asn Gly
                20                  25                  30

AGA GTG CCG GTG CTG AGA CCC TTG AAG TGC ATC CCT GCG AGC AAG AAG     144
Arg Val Pro Val Leu Arg Pro Leu Lys Cys Ile Pro Ala Ser Lys Lys
            35                  40                  45

ACA GAT CCG CAG AAG GAC CTT AAG CCT GCC CCG CAG CAG TGT CGC CTG     192
Thr Asp Pro Gln Lys Asp Leu Lys Pro Ala Pro Gln Gln Cys Arg Leu
        50                  55                  60

CCC ACC ATA GTG CGG AAA GGC GGA AGA TAA                             222
Pro Thr Ile Val Arg Lys Gly Gly Arg
 65                  70
```

(2) INFORMATION FOR SEQ ID NO:5:

(i) SEQUENCE CHARACTERISTICS:
            (A) LENGTH: 73 amino acids
            (B) TYPE: amino acid
            (D) TOPOLOGY: linear (ii) MOLECULE TYPE: protein (xi) SEQUENCE DESCRIPTION: SEQ ID NO:5:

```
Met Glu Leu Pro Lys Leu Lys Leu Ser Gly Val Val Arg Leu Ser Ser
 1               5                  10                  15

Tyr Ser Ser Pro Thr Leu Gln Ser Val Leu Gly Ser Gly Thr Asn Gly
                20                  25                  30

Arg Val Pro Val Leu Arg Pro Leu Lys Cys Ile Pro Ala Ser Lys Lys
            35                  40                  45

Thr Asp Pro Gln Lys Asp Leu Lys Pro Ala Pro Gln Gln Cys Arg Leu
        50                  55                  60

Pro Thr Ile Val Arg Lys Gly Gly Arg
 65                  70
```

(2) INFORMATION FOR SEQ ID NO:6:

(i) SEQUENCE CHARACTERISTICS:
            (A) LENGTH: 123 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (v) FRAGMENT TYPE: internal (vi) ORIGINAL SOURCE:
            (A) ORGANISM: Homo sapiens (ix) FEATURE:
            (A) NAME/KEY: CDS
            (B) LOCATION: 1..123

(xi) SEQUENCE DESCRIPTION: SEQ ID NO:6:

| ATG | TCA | TCG | GCA | CAC | CCG | CTC | AGA | AGA | TCC | TCA | CCA | AGT | TCA | AAC | AGG | 48 |
| Met | Ser | Ser | Ala | His | Pro | Leu | Arg | Arg | Ser | Ser | Pro | Ser | Ser | Asn | Arg | |
| 1 | | | | 5 | | | | | 10 | | | | | 15 | | |

| ATC | AGG | AAT | ACC | TCT | ACT | AAC | AAC | CAA | TTT | GTC | CCC | ACA | ATG | CCT | CTC | 96 |
| Ile | Arg | Asn | Thr | Ser | Thr | Asn | Asn | Gln | Phe | Val | Pro | Thr | Met | Pro | Leu | |
| | | | 20 | | | | | 25 | | | | | 30 | | | |

| CCT | CCT | GCA | CGC | AAT | GGT | GGC | CTA | TGA | | | | | | | | 123 |
| Pro | Pro | Ala | Arg | Asn | Gly | Gly | Leu | | | | | | | | | |
| | | 35 | | | | 40 | | | | | | | | | | |

(2) INFORMATION FOR SEQ ID NO:7:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:7:

Met Ser Ser Ala His Pro Leu Arg Arg Ser Ser Pro Ser Ser Asn Arg
1               5                   10                  15

Ile Arg Asn Thr Ser Thr Asn Asn Gln Phe Val Pro Thr Met Pro Leu
            20                  25                  30

Pro Pro Ala Arg Asn Gly Gly Leu
        35                  40

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:8:

GTGTCTCCTT CGTCTCTACT A        21

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:9:

GGTGTGCCGA TGACATCG        18

(2) INFORMATION FOR SEQ ID NO:10:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: YES (vi) ORIGINAL SOURCE:
             (A) ORGANISM: Homo sapiens (xi) SEQUENCE DESCRIPTION: SEQ ID NO:10:

```
GAGGTATTCC TGATCCTG                                                   18
```

(2) INFORMATION FOR SEQ ID NO:11:

(i) SEQUENCE CHARACTERISTICS:
             (A) LENGTH: 1168 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (vi) ORIGINAL SOURCE:
             (A) ORGANISM: Homo sapiens (xi) SEQUENCE DESCRIPTION: SEQ ID NO:11:

```
CTGTGACTGG TGCTGGAGTT TTGAGTCCAC AGATAAAATG TGTCTCCTTC GTCTCTACTA     60

GAGAGGAAAA AGAACTGGAA TTGGAAGAAC AGGGAGACTG AAGGGTAGCA AGAGAGGCTG    120

GAGAAGAGAG TGAAAAGACC GCTTACCTGA TTTGAAATTG TCTGCAGCCC CTCTTTCCTG    180

GAGTAAATGA ACTGGACCAA ATCTCAAAAA TCCACGATGT CATCGGCACA CCCGCTCAGA    240

AGATCCTCAC CAAGTTCAAA CAGTCGAGAG CTATGAATTT TGATTTTCCT TTTAAAAAGG    300

GATCAGGAAT ACCTCTACTA ACAACCAATT TGTCCCCACA ATGCCTCTCC CTCCTGCACG    360

CAATGGTGGC CTATGATCCC GATGAGAGAA TCGCCGCCCA CCAGGCCCTG CAGCACCCCT    420

ACTTCCAAGA ACAGAGAAAC AGTCCCTAAA GCAAGAGGAG GACCGTCCCA AGAGACGAGG    480

ACCGGCCTAT GTCATGGAAC TGCCCAAACT AAAGCTTTCG GGAGTGGTCA GACTGTCGTC    540

TTACTCCAGC CCCACGCTGC AGTCCGTGCT TGGATCTGGA ACAAATGGAA GAGTGCCGGT    600

GCTGAGACCC TTGAAGTGCA TCCCTGCGAG CAAGAAGACA GATCCGCAGA AGGACCTTAA    660

GCCTGCCCCG CAGCAGTGTC GCCTGCCCAC CATAGTGCGG AAAGGCGGAA GATAACTGAG    720

CAGCACCGTC GTCTCGACTT CGGAGGCAAC ACCAAGCCCG ACCGGGCCAG GCCTGGGTGA    780

TCTGCTGCTG AGACGCCACG GAGGGCTGGG GATGCGCCTG CGTCCGTTTC GCGCTGGCCG    840

GGGCTCTGGG TGCTGCCCTG CGCCCTGCCG CACCCGCGGC CCGCGCAGCT GCCTAGGATG    900

TTCTGGGCTA ATATACTTGT AAAACCACCG CATTCTAGGG TTTTCTTTCA TTTTCGTTAA    960

GAATTTGGGG CAGGAAATAC TTTGTAACTT TGTATATGAA TCAAAACAAA CGAGCAGGCA   1020

TTTCTGTGAT GTGTTGGGCG TGGTTGGAAG GTGGGTTCTG CGTGTCCCTT CCCAGCGCTG   1080

CTGGTCAGTC GTGGAGCGCC ATCATGTCTT ACCAGTGACG CTGCTGACAC CCCTGACTTT   1140

TATTAAAGAA TAAGCTGTCG TTAAAAAA                                     1168
```

(2) INFORMATION FOR SEQ ID NO:12:

(i) SEQUENCE CHARACTERISTICS:
        (A) LENGTH: 1235 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:12:

```
ATTCCTGAGT CTGTGACTGG TGCTGGAGTT TTGAGTCCAC AGATAAAATG TGTCTCCTTC        60

GTCTCTACTA GAGAGGAAAA AGAACTGGAA TTGGAAGAAC AGGGAGACTG AAGGGTAGCA       120

AGAGAGGCTG GAGAAGAGAG TGAAAAGACC GCTTACCTGA TTTGAAATTG ATGGTGGCGT       180

GGGAATGAAG AATGTGATAT ACATCTTTGG AGTCTGTTCT GCAGCCCCTC TTTCCTGGAG       240

TAAATGAACT GGACCAAATC TCAAAAATCC ACGATGTCAT CGGCACACCC GCTCAGAAGA       300

TCCTCACCAA GTTCAAACAG TCGAGAGCTA TGAATTTTGA TTTTCCTTTT AAAAAGGGAT       360

CAGGAATACC TCTACTAACA ACCAATTTGT CCCCACAATG CCTCTCCCTC CTGCACGCAA       420

TGGTGGCCTA TGATCCCGAT GAGAGAATCG CCGCCCACCA GGCCCTGCAG CACCCCTACT       480

TCCAAGAACA GAGAAACAGT CCCTAAAGCA AGAGGAGGAC CGTCCCAAGA GACGAGGACC       540

GGCCTATGTC ATGGAACTGC CCAAACTAAA GCTTTCGGGA GTGGTCAGAC TGTCGTCTTA       600

CTCCAGCCCC ACGCTGCAGT CCGTGCTTGG ATCTGGAACA AATGGAAGAG TGCCGGTGCT       660

GAGACCCTTG AAGTGCATCC CTGCGAGCAA GAAGACAGAT CCGCAGAAGG ACCTTAAGCC       720

TGCCCCGCAG CAGTGTCGCC TGCCCACCAT AGTGCGGAAA GGCGGAAGAT AACTGAGCAG       780

CACCGTCGTC TCGACTTCGG AGGCAACACC AAGCCCGACC GGGCCAGGCC TGGGTGATCT       840

GCTGCTGAGA CGCCACGGAG GGCTGGGGAT GCGCCTGCGT CCGTTTCGCG CTGGCCGGGG       900

CTCTGGGTGC TGCCCTGCGC CCTGCCGCAC CCGCGGCCCG CGCAGCTGCC TAGGATGTTC       960

TGGGCTAATA TACTTGTAAA ACCACCGCAT TCTAGGGTTT TCTTTCATTT TCGTTAAGAA      1020

TTTGGGGCAG GAAATACTTT GTAACTTTGT ATATGAATCA AAACAAACGA GCAGGCATTT      1080

CTGTGATGTG TTGGGCGTGG TTGGAAGGTG GGTTCTGCGT GTCCCTTCCC AGCGCTGCTG      1140

GTCAGTCGTG GAGCGCCATC ATGTCTTACC AGTGACGCTG CTGACACCCC TGACTTTTAT      1200

TAAAGAATAA GCTGTCGTTA CAGTATTGCA AAAA                                  1235
```

(2) INFORMATION FOR SEQ ID NO:13:

(i) SEQUENCE CHARACTERISTICS:
        (A) LENGTH: 2051 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:13:

```
GACTGGTGCT GGAGTTTTGA GTCCACAGAT AAAATGTGTC TCCTTCGTCT CTACTAGAGA        60

GGAAAAAGAA CTGGAATTGG AAGAACAGGG AGACTGAAGG GTAGCAAGAG AGGCTGGAGA       120

AGAGAGTGAA AAGACCGCTT ACCTGATTTG AAATTGTCTG CAGCCCCTCT TTCCTGGAGT       180
```

```
AAATGAACTG GACCAAATCT CAAAAATCCA CGATGTCATC GGCACACCCG CTCAGAAGAT      240

CCTCACCAAG TTCAAACAGT CGAGAGCTAT GAATTTTGAT TTTCCTTTTA AAAAGGGATC      300

AGGAATACCT CTACTAACAA CCAATTTGTC CCCACAATGC CTCTCCCTCC TGCACGCAAT      360

GGTGGCCTAT GATCCCGATG AGAGAATCGC CGCCCACCAG GCCCTGCAGC ACCCCTACTT      420

CCAAGAACAG AGAACCCAGA ACGGAAGCGA GGATGAAGGC CTCAGCCGTC CTCCTCCCCA      480

TTCAAACACG TTCATCCCTC AACCCTCTGC TGAGCACCTG CATGCTGCCC GGCCGCAGTG      540

TCACCCTTCT TGTGTGAGCC TACCCTCATC CACCCACCTC ACCCTCCTGA CCTTAAAGAA      600

GACACCGGGC AGAAGCACAG GGGAGCCCAG TCACACCCCA CACTGGCGGG GGCAGGCCTT      660

GCAGGGAGAA GCAGTAAGCA GCCATCTCCA TCAGCCATTT CCATCTGGCA CTCAGACGTG      720

CACGTCTTCG TGTGACAGGC GGCAGCAGTG CGACCGTGAC CTCCCATCTG CTCTGCTGTC      780

CCCACACCTG CGGTGCAGCC AGCCTGCCAC AAGGCAGCTA GAGTCCAGCT AGACCCACCC      840

CTGGCACGGC CGACCTCTTC CTGGCTTCTT CTGGGCCTAA TCCCCGTGCA TTCTCCAACG      900

CCAGAAGTGT AAGAAAGTGC AAGGCAACAA GTGAGAAGAG CAAACCCAAA TCGTACCAGG      960

GAAGCTAGTC TTTCCAGGGC ACCTGAGTGA GGGCATGACC AGCCTTGACG CTGCCTCGCT     1020

ACCATCTGCC CAGGGCCTGC TGAATGCTTG AGTCCATGGT GACAGTGGTG GGAACAGTTA     1080

CGAGGCAGTT AGATTTTGGA AGTCATGTTG GCCCACTTGG CTACAGAGCA GTCTTAGGAA     1140

CAGCACCATA AAAATAAAGA CTTATTCCTG ACACACATGC ATCTAGAGTA AACTGGGGCG     1200

TATCTGACAG CGTTAGTACA GTGATGGCCA AATGCAAACT GCATTCCAGA ACCAGCGAAG     1260

GGTGACAGAC TGGGCTGAGG CAGAGCTAGG ACTAACCATC TCGAGTGATG CCATCTCGGG     1320

GCCAACAAAA GTTTTGGACA CGGCTGGATC ATCTGACCAA ACTGCTCAAA TCTTTACACA     1380

ATTATTGTCC TGGTATTAAA CTTTCACCTG CCACTTCCAA CAAACAGGAG ACAGAATAAG     1440

GAGATGACCA GGAAGATGGC TGGATTAAGA ATTCTAGACT TGGCCGGGTG CGGTGGCTCA     1500

CACCTGTAAT CCTAGCATCT TGGGAGGCTG AGGCAGGAGG ATCGCTTGAG CCCAGAGTTT     1560

GAGACCAGCC TAGGCAACAT AAGGAGACCC CATCTCTACA AAATATCAAA AAATTACCCA     1620

GGTATGGTGG CACACACGTG TGATTCCAGC TACTCGGGAG GCTGAGATGG GAGGATCACT     1680

TGAACCCAGG AGGTTGGGGC TACAATGAGC TATGATCGCA CCACTTCATT CCAGCCTGGA     1740

TGACAGAAGA CTCACTCCAT AGTTCATGGC CCCGTGATCC AGAGTCCCTG CTGGCGCCTT     1800

CGAGTGGGGC AGGCTGAGAA CTCAAGCTGT AACTAATGTC TCCTCCGAAG AAAACTAAAC     1860

CGAGGGCTGA GCTGATGTGA AGTTTTCCGT GGCTGCATTC ATACAAATGG TGAAAATGTA     1920

GCATACCTCC CCTCAAAAGC CTGAAAGTAA AGACATGCCC CCAATTTAAT GTGATGAATT     1980

AGAGAAATAG GTTTCAGACA CTTCATGGTT TAAAGTCTCA CAAAATAAAG CTTTCGAAGG     2040

AAAAAAAAA A                                                          2051
```

(2) INFORMATION FOR SEQ ID NO:14:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (ix) FEATURE:
    (A) NAME/KEY: CDS
    (B) LOCATION: 1..90

(xi) SEQUENCE DESCRIPTION: SEQ ID NO:14:

```
ATG AAC TGG ACC AAA TCT CAA AAA TCC ACG ATG TCA TCG GCA CAC CCG     48
Met Asn Trp Thr Lys Ser Gln Lys Ser Thr Met Ser Ser Ala His Pro
 1               5                  10                  15

CTC AGA AGA TCC TCA CCA AGT TCA AAC AGT CGA GAG CTA TGA             90
Leu Arg Arg Ser Ser Pro Ser Ser Asn Ser Arg Glu Leu
            20                  25                  30
```

(2) INFORMATION FOR SEQ ID NO:15:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asn Trp Thr Lys Ser Gln Lys Ser Thr Met Ser Ser Ala His Pro
 1               5                  10                  15

Leu Arg Arg Ser Ser Pro Ser Ser Asn Ser Arg Glu Leu
            20                  25
```

(2) INFORMATION FOR SEQ ID NO:16:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (ix) FEATURE:
        (A) NAME/KEY: CDS
        (B) LOCATION: 1..177

(xi) SEQUENCE DESCRIPTION: SEQ ID NO:16:

```
ATG AAT TTT GAT TTT CCT TTT AAA AAG GGA TCA GGA ATA CCT CTA CTA     48
Met Asn Phe Asp Phe Pro Phe Lys Lys Gly Ser Gly Ile Pro Leu Leu
 1               5                  10                  15

ACA ACC AAT TTG TCC CCA CAA TGC CTC TCC CTC CTG CAC GCA ATG GTG     96
Thr Thr Asn Leu Ser Pro Gln Cys Leu Ser Leu Leu His Ala Met Val
            20                  25                  30

GCC TAT GAT CCC GAT GAG AGA ATC GCC GCC CAC CAG GCC CTG CAG CAC    144
Ala Tyr Asp Pro Asp Glu Arg Ile Ala Ala His Gln Ala Leu Gln His
        35                  40                  45

CCC TAC TTC CAA GAA CAG AGA AAC AGT CCC TAA                        177
Pro Tyr Phe Gln Glu Gln Arg Asn Ser Pro
 50                  55
```

(2) INFORMATION FOR SEQ ID NO:17:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asn Phe Asp Phe Pro Phe Lys Lys Gly Ser Gly Ile Pro Leu Leu
  1               5                  10                  15

Thr Thr Asn Leu Ser Pro Gln Cys Leu Ser Leu Leu His Ala Met Val
             20                  25                  30

Ala Tyr Asp Pro Asp Glu Arg Ile Ala Ala His Gln Ala Leu Gln His
         35                  40                  45

Pro Tyr Phe Gln Glu Gln Arg Asn Ser Pro
     50                  55
```

(2) INFORMATION FOR SEQ ID NO:18:

(i) SEQUENCE CHARACTERISTICS:
        (A) LENGTH: 564 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (ix) FEATURE:
        (A) NAME/KEY: CDS
        (B) LOCATION: 1..564

(xi) SEQUENCE DESCRIPTION: SEQ ID NO:18:

```
ATG AAT TTT GAT TTT CCT TTT AAA AAG GGA TCA GGA ATA CCT CTA CTA      48
Met Asn Phe Asp Phe Pro Phe Lys Lys Gly Ser Gly Ile Pro Leu Leu
  1               5                  10                  15

ACA ACC AAT TTG TCC CCA CAA TGC CTC TCC CTC CTG CAC GCA ATG GTG      96
Thr Thr Asn Leu Ser Pro Gln Cys Leu Ser Leu Leu His Ala Met Val
             20                  25                  30

GCC TAT GAT CCC GAT GAG AGA ATC GCC GCC CAC CAG GCC CTG CAG CAC     144
Ala Tyr Asp Pro Asp Glu Arg Ile Ala Ala His Gln Ala Leu Gln His
         35                  40                  45

CCC TAC TTC CAA GAA CAG AGA ACC CAG AAC GGA AGC GAG GAT GAA GGC     192
Pro Tyr Phe Gln Glu Gln Arg Thr Gln Asn Gly Ser Glu Asp Glu Gly
     50                  55                  60

CTC AGC CGT CCT CCT CCC CAT TCA AAC ACG TTC ATC CCT CAA CCC TCT     240
Leu Ser Arg Pro Pro Pro His Ser Asn Thr Phe Ile Pro Gln Pro Ser
 65                  70                  75                  80

GCT GAG CAC CTG CAT GCT GCC CGG CCG CAG TGT CAC CCT TCT TGT GTG     288
Ala Glu His Leu His Ala Ala Arg Pro Gln Cys His Pro Ser Cys Val
                 85                  90                  95

AGC CTA CCC TCA TCC ACC CAC CTC ACC CTC CTG ACC TTA AAG AAG ACA     336
Ser Leu Pro Ser Ser Thr His Leu Thr Leu Leu Thr Leu Lys Lys Thr
            100                 105                 110

CCG GGC AGA AGC ACA GGG GAG CCC AGT CAC ACC CCA CAC TGG CGG GGG     384
Pro Gly Arg Ser Thr Gly Glu Pro Ser His Thr Pro His Trp Arg Gly
        115                 120                 125

CAG GCC TTG CAG GGA GAA GCA GTA AGC AGC CAT CTC CAT CAG CCA TTT     432
Gln Ala Leu Gln Gly Glu Ala Val Ser Ser His Leu His Gln Pro Phe
    130                 135                 140

CCA TCT GGC ACT CAG ACG TGC ACG TCT TCG TGT GAC AGG CGG CAG CAG     480
Pro Ser Gly Thr Gln Thr Cys Thr Ser Ser Cys Asp Arg Arg Gln Gln
145                 150                 155                 160

TGC GAC CGT GAC CTC CCA TCT GCT CTG CTG TCC CCA CAC CTG CGG TGC     528
Cys Asp Arg Asp Leu Pro Ser Ala Leu Leu Ser Pro His Leu Arg Cys
                165                 170                 175
```

```
AGC CAG CCT GCC ACA AGG CAG CTA GAG TCC AGC TAG                              564
Ser Gln Pro Ala Thr Arg Gln Leu Glu Ser Ser
        180                 185
```

(2) INFORMATION FOR SEQ ID NO:19:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO:19:

```
Met Asn Phe Asp Phe Pro Phe Lys Lys Gly Ser Gly Ile Pro Leu Leu
 1               5                  10                  15

Thr Thr Asn Leu Ser Pro Gln Cys Leu Ser Leu His Ala Met Val
            20                  25                  30

Ala Tyr Asp Pro Asp Glu Arg Ile Ala Ala His Gln Ala Leu Gln His
            35                  40                  45

Pro Tyr Phe Gln Glu Gln Arg Thr Gln Asn Gly Ser Glu Asp Glu Gly
        50                  55                  60

Leu Ser Arg Pro Pro His Ser Asn Thr Phe Ile Pro Gln Pro Ser
65              70                  75                  80

Ala Glu His Leu His Ala Ala Arg Pro Gln Cys His Pro Ser Cys Val
            85                  90                  95

Ser Leu Pro Ser Ser Thr His Leu Thr Leu Leu Thr Leu Lys Lys Thr
            100                 105                 110

Pro Gly Arg Ser Thr Gly Glu Pro Ser His Thr Pro His Trp Arg Gly
            115                 120                 125

Gln Ala Leu Gln Gly Glu Ala Val Ser Ser His Leu His Gln Pro Phe
130                 135                 140

Pro Ser Gly Thr Gln Thr Cys Thr Ser Ser Cys Asp Arg Arg Gln Gln
145                 150                 155                 160

Cys Asp Arg Asp Leu Pro Ser Ala Leu Leu Ser Pro His Leu Arg Cys
                165                 170                 175

Ser Gln Pro Ala Thr Arg Gln Leu Glu Ser Ser
        180                 185
```

(2) INFORMATION FOR SEQ ID NO:20:

(i) SEQUENCE CHARACTERISTICS:
        (A) LENGTH: 189 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (ix) FEATURE:
        (A) NAME/KEY: CDS
        (B) LOCATION: 1..189

(xi) SEQUENCE DESCRIPTION: SEQ ID NO:20:

```
ATG ATC CCG ATG AGA GAA TCG CCG CCC ACC AGG CCC TGC AGC ACC CCT              48
Met Ile Pro Met Arg Glu Ser Pro Pro Thr Arg Pro Cys Ser Thr Pro
 1               5                  10                  15
```

```
ACT TCC AAG AAC AGA GAA CCC AGA ACG GAA GCG AGG ATG AAG GCC TCA        96
Thr Ser Lys Asn Arg Glu Pro Arg Thr Glu Ala Arg Met Lys Ala Ser
         20                  25                  30

GCC GTC CTC CTC CCC ATT CAA ACA CGT TCA TCC CTC AAC CCT CTG CTG       144
Ala Val Leu Leu Pro Ile Gln Thr Arg Ser Ser Leu Asn Pro Leu Leu
         35                  40                  45

AGC ACC TGC ATG CTG CCC GGC CGC AGT GTC ACC CTT CTT GTG TGA           189
Ser Thr Cys Met Leu Pro Gly Arg Ser Val Thr Leu Leu Val
         50                  55                  60
```

(2) INFORMATION FOR SEQ ID NO:21:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:21:

```
Met Ile Pro Met Arg Glu Ser Pro Pro Thr Arg Pro Cys Ser Thr Pro
 1               5                  10                  15

Thr Ser Lys Asn Arg Glu Pro Arg Thr Glu Ala Arg Met Lys Ala Ser
         20                  25                  30

Ala Val Leu Leu Pro Ile Gln Thr Arg Ser Ser Leu Asn Pro Leu Leu
         35                  40                  45

Ser Thr Cys Met Leu Pro Gly Arg Ser Val Thr Leu Leu Val
         50                  55                  60
```

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Homo sapiens (xi) SEQUENCE DESCRIPTION: SEQ ID NO:22:

```
Ser Pro Ser Ser Asn Arg Ile Arg Asn Thr Ser Thr
 1               5                  10
```

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Homo sapiens (xi) SEQUENCE DESCRIPTION: SEQ ID NO:23:

```
Ser Pro Ser Ser Asn Arg Ile Arg Asn
 1               5
```

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Homo sapiens (xi) SEQUENCE DESCRIPTION: SEQ ID NO:24:

Pro Ser Ser Asn Arg Ile Arg Asn Thr
1               5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Homo sapiens (xi) SEQUENCE DESCRIPTION: SEQ ID NO:25:

Ser Ser Asn Arg Ile Arg Asn Thr Ser
1               5

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Homo sapiens (xi) SEQUENCE DESCRIPTION: SEQ ID NO:26:

Ser Pro Ser Ser Asn Arg Ile Arg Asn Thr
1               5                   10

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:27:

TCACCAAGTT CAAACAGGAT CAGGAAT                                            27

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:28:

TCACCAAGTT CAAACAGGAT CAGGAATACC        30

(2) INFORMATION FOR SEQ ID NO:29:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (ix) FEATURE:
        (A) NAME/KEY: Region
        (B) LOCATION: 7
        (D) OTHER INFORMATION: /note= "N = a nucleotide insert"

(xi) SEQUENCE DESCRIPTION: SEQ ID NO:29:

CAAACANGGA TCA        13

(2) INFORMATION FOR SEQ ID NO:30:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: Region
        (B) LOCATION: 1
        (D) OTHER INFORMATION: /note= "N = zero, one or more
        contiguous nucleotides"

(xi) SEQUENCE DESCRIPTION: SEQ ID NO:30:

NTATTCCTGA TCCT        14

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: Region
        (B) LOCATION: 1
        (D) OTHER INFORMATION: /note= "N = zero, one or more
            contiguous nucleotides"

(xi) SEQUENCE DESCRIPTION: SEQ ID NO:31:

NTATTCCTGA TCCTG                                                          15

(2) INFORMATION FOR SEQ ID NO:32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: Region
        (B) LOCATION: 1
        (D) OTHER INFORMATION: /note= "N = zero, one or more
            contiguous nucleotides"

(xi) SEQUENCE DESCRIPTION: SEQ ID NO:32:

NTATTCCTGA TCCTGT                                                         16

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: Region
        (B) LOCATION: 1
        (D) OTHER INFORMATION: /note= "N = zero, one or more
            contiguous nucleotides"

(xi) SEQUENCE DESCRIPTION: SEQ ID NO:33:

NTATTCCTGA TCCTGTT                                                        17

(2) INFORMATION FOR SEQ ID NO:34:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: Region
        (B) LOCATION: 1
        (D) OTHER INFORMATION: /note= "N = zero, one or more contiguous nucleotides"

(xi) SEQUENCE DESCRIPTION: SEQ ID NO:34:

NCAAGTTCAA ACAG                                              14

(2) INFORMATION FOR SEQ ID NO:35:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: Region
      (B) LOCATION: 1
      (D) OTHER INFORMATION: /note= "N = zero, one or more
         contiguous nucleotides"

(xi) SEQUENCE DESCRIPTION: SEQ ID NO:35:

NCAAGTTCAA ACAGG                                             15

(2) INFORMATION FOR SEQ ID NO:36:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: Region
      (B) LOCATION: 1
      (D) OTHER INFORMATION: /note= "N = zero, one or more
         contiguous nucleotides"

(xi) SEQUENCE DESCRIPTION: SEQ ID NO:36:

NCAAGTTCAA ACAGGA                                            16

(2) INFORMATION FOR SEQ ID NO:37:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: Region
      (B) LOCATION: 1
      (D) OTHER INFORMATION: /note= "N = zero, one or more
         contiguous nucleotides"

(xi) SEQUENCE DESCRIPTION: SEQ ID NO:37:

NCAAGTTCAA ACAGGAT                                           17